(12) United States Patent  
Sakurai et al.

(10) Patent No.: US 7,063,692 B2  
(45) Date of Patent: Jun. 20, 2006

(54) SURGICAL OPERATION SYSTEM

(75) Inventors: Tomohisa Sakurai, Sagamihara (JP); Hiroyuki Takahashi, Akishima (JP); Masaru Sudo, Hachioji (JP); Takeaki Nakamura, Hino (JP); Keiji Shioda, Hachioji (JP); Takashi Ozaki, Hachioji (JP); Makoto Miyawaki, Tanashi (JP)

(73) Assignee: Olympus Corporation, Tokyo (JP)

( * ) Notice: Subject to any disclaimer, the term of this patent is extended or adjusted under 35 U.S.C. 154(b) by 252 days.

(21) Appl. No.: 10/628,628

(22) Filed: Jul. 28, 2003

(65) Prior Publication Data

US 2004/0019347 A1    Jan. 29, 2004

Related U.S. Application Data

(62) Division of application No. 09/794,864, filed on Feb. 27, 2001, now Pat. No. 6,623,423.

(30) Foreign Application Priority Data

Feb. 29, 2000  (JP)  ............... 2000-54181  
Mar. 29, 2000  (JP)  ............... 2000-91904  
Feb. 16, 2001  (JP)  ............... 2001-40501

(51) Int. Cl.  
*A61B 17/00* (2006.01)

(52) U.S. Cl. ............... 606/1; 600/101; 600/131

(58) Field of Classification Search ............... 606/1, 606/10, 34, 46, 167, 170, 180; 600/101, 600/104, 105, 131, 113  
See application file for complete search history.

(56) References Cited

U.S. PATENT DOCUMENTS 6,017,354 A      1/2000  Culp et al.  
6,899,538 B1 *  5/2005  Matoba ............... 433/114

FOREIGN PATENT DOCUMENTS

| JP | 6-296589 | 10/1994 |
| JP | 8-164148 | 6/1996 |
| JP | 9-38098 | 2/1997 |
| JP | 11-318916 | 11/1999 |
| JP | 11-318935 | 11/1999 |
| JP | 2000-271135 | 10/2000 |

* cited by examiner

*Primary Examiner*—Beverly M. Flanagan  
(74) *Attorney, Agent, or Firm*—Scully, Scott, Murphy & Presser, P.C.

(57) ABSTRACT

A plurality of handpieces used to perform an operation is connected to a main operation apparatus, which generates a driving signal, through connectors formed on the main apparatus. When an operator holds a handpiece he/she wants to use, an output line over which the driving signal is transmitted is routed to the held handpiece owing to an output of a sensor that detects a change in capacitance stemming from the hold. The operator therefore need not manually set a mode in which the driving signal is applied to the handpiece he/she wants to use. Moreover, a port number assigned to a port to which the output line is routed is indicated on a display device. The operator can readily identify the usable handpiece.

8 Claims, 21 Drawing Sheets

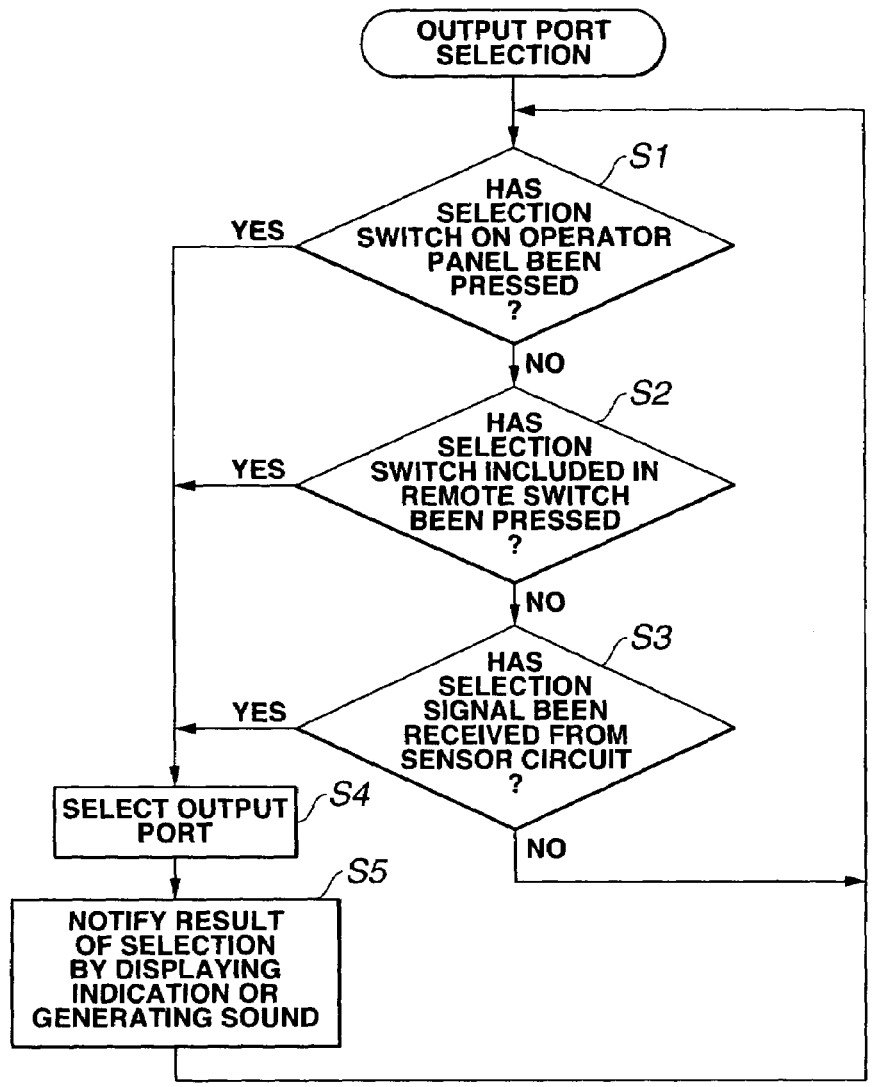
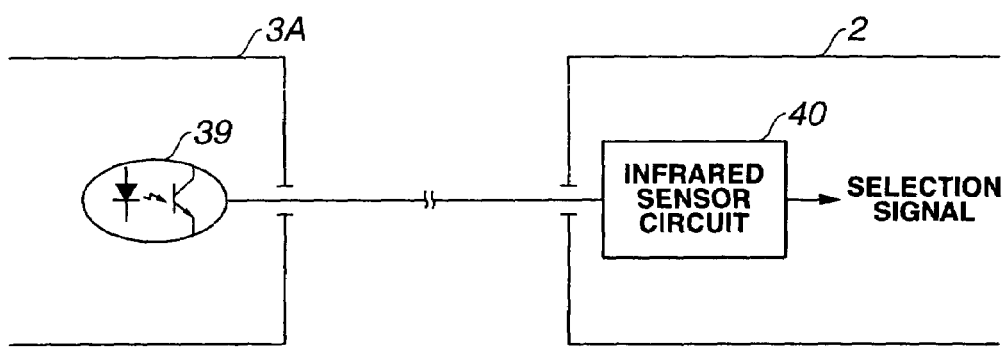

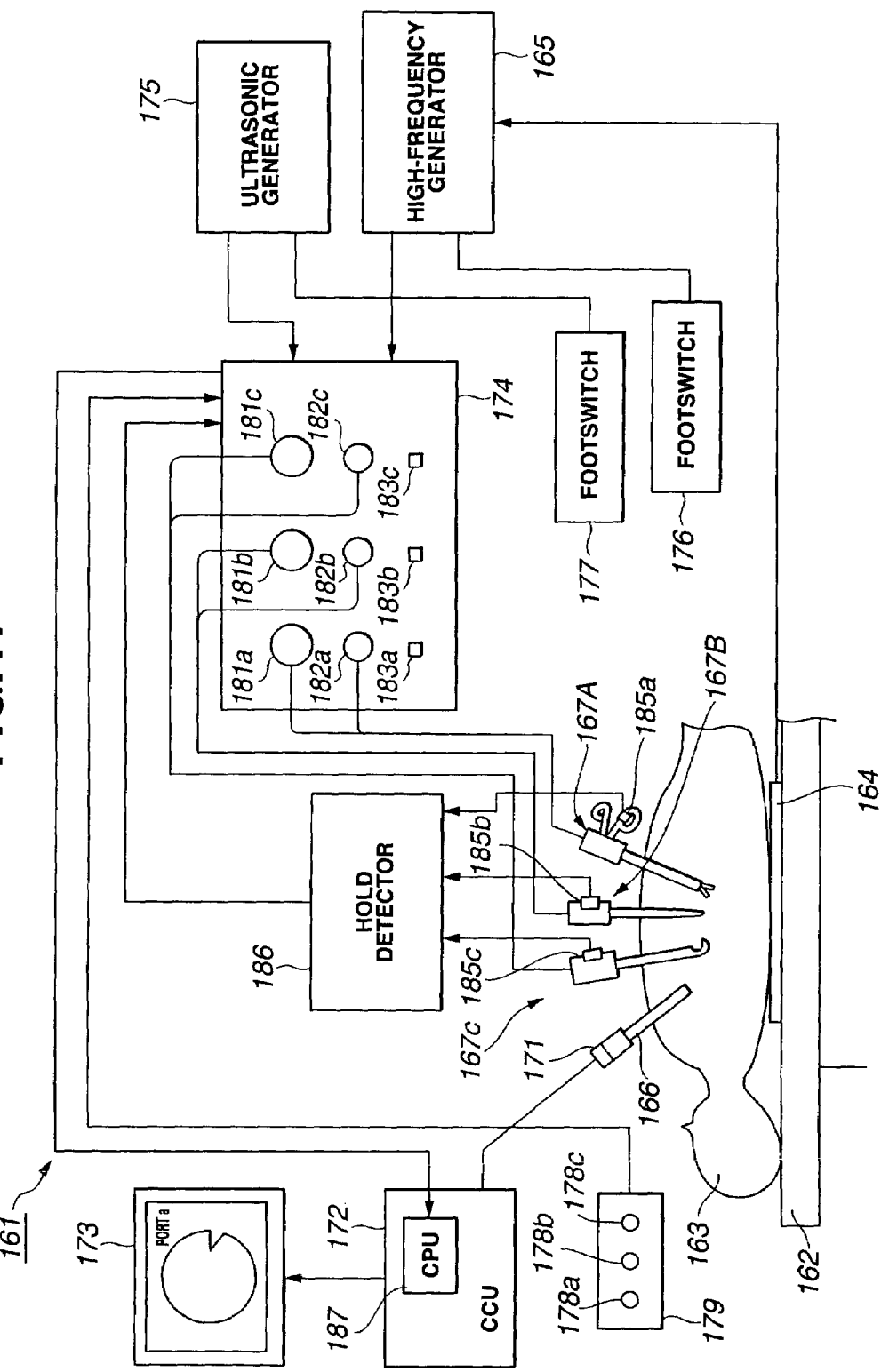

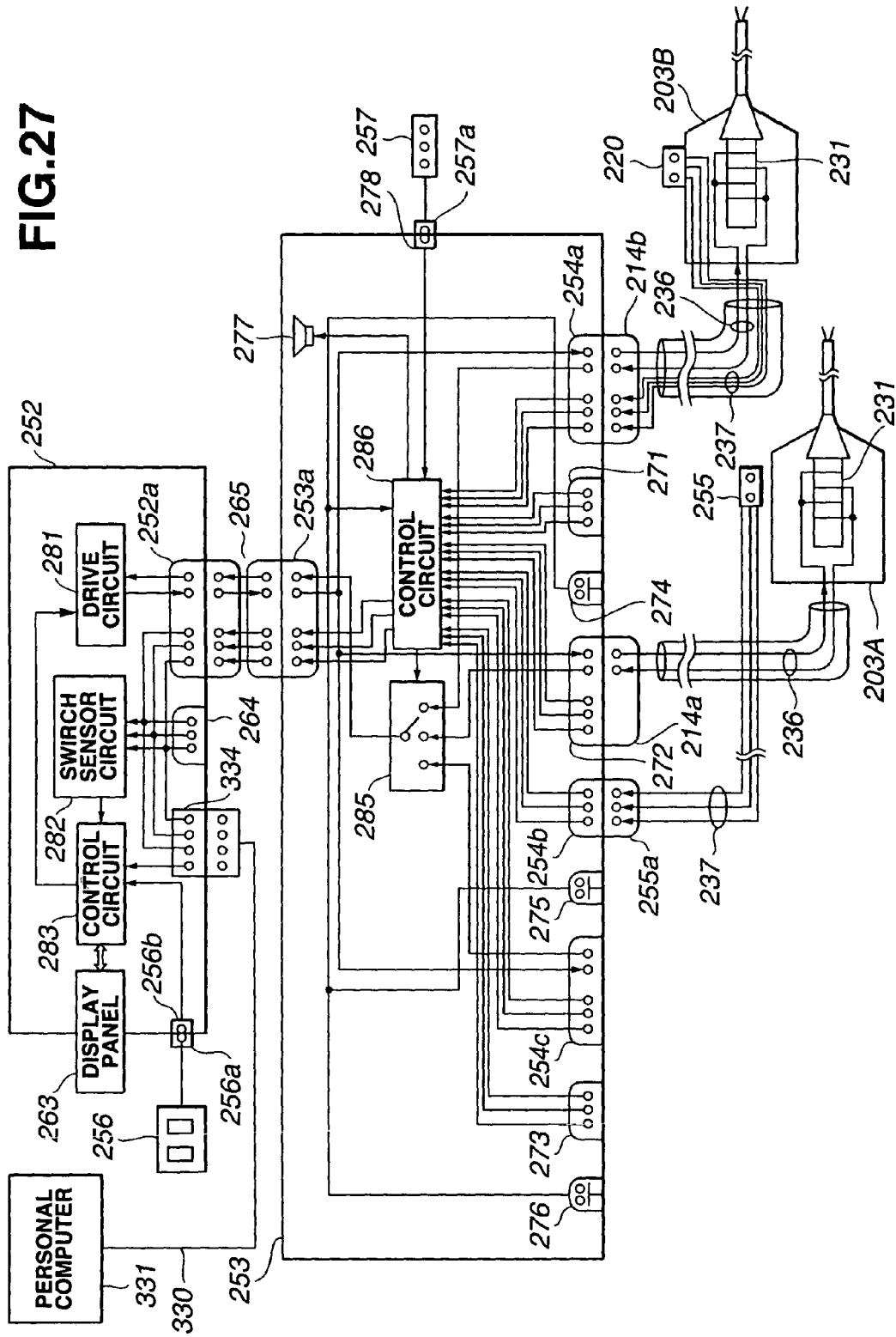

SURGICAL OPERATION SYSTEM

The present application cites the basic applications of Japanese Patent Application No. 2000-54181 (filed on Feb. 29, 2000), Japanese Patent Application No. 2000-40501 (filed on Feb. 16, 2001) claiming the priority of the application No. 2000-54181, and Japanese Patent Application No. 2000-91904 (filed on Mar. 29, 2000), and enjoys the benefits of the applications. This application is a divisional of U.S. application Ser. No. 09/794,864, filed Feb. 27, 2001 now U.S. Pat. No. 6,623,423.

BACKGROUND OF THE INVENTION

1. Field of the Invention

The present invention relates to a surgical operation system including a plurality of handpieces. Herein, when a handpiece to be used is selected by holding the handpiece, routes of an output line over which a driving signal is applied to the handpiece are switched, and information of the selected handpiece is notified.

2. Description of the Related Art

Ultrasonic knife systems including the one described in, for example, Japanese Patent Application No. 11-269242 (filed on Sep. 22, 1999) have been proposed as surgical operation systems.

With the prevalence of the operation system, an increasing number of types of handpieces have come to be used for operations. If a plurality of handpieces suitable for an operation can be connected to one operating apparatus, the plurality of handpieces is changed for use during a surgical procedure.

In this type of system, for changing a plurality of handpieces, it is necessary to manipulate a change switch on a front panel of a main apparatus. Otherwise, a dedicated remote switch is needed to change handpieces.

However, when the change switch on the front panel must be used to change handpieces, since the main apparatus is installed in a filthy zone within an operating room, an operator who performs an operation cannot manipulate the change switch. The operator must ask a nurse or the like to manipulate the change switch. The operator may find this annoying.

Moreover, when the remote switch must be used to change handpieces, the switch on which an operator steps must be installed in a clean operating zone. This leads to an increase in the number of switches with a cord installed in the operating zone. Better maneuverability is demanded.

Moreover, when a plurality of handpieces is used during a surgical procedure, a handpiece changing means is needed to change the plurality of connected handpieces.

When a plurality of handpieces is connected so that any of the handpieces can be selected, an operator has difficulty in identifying a handpiece the operator now holds.

SUMMARY OF THE INVENTION

An object of the present invention to provide a surgical operation system capable of offering excellent maneuverability and outputting treatment energy from a held handpiece out of a plurality of connected handpiece once an operator actually holds the handpiece.

Another object of the present invention is to provide a surgical operation system enabling an operator to identify a handpiece the operator has now selected even when a plurality of handpieces can be connected to be able to be selected.

Still another object of the present invention is to provide a user-friendly endoscopic operation system making it possible to check information of a selected handpiece with an endoscopic image viewed during an operation under endoscopic observation.

Still another object of the present invention is to provide a surgical operation system that enables remote control despite its simple configuration and that is easy to use and user-friendly because an operator is visually informed of a handpiece the operator has selected and whether the handpiece is outputting energy.

According to the present invention, a surgical operation system consists mainly of a plurality of handpieces, a driving signal generator, an output switching unit, hand-held members, hold detecting devices, and an output switching control unit. The plurality of handpieces generates predetermined energies. The driving signal generator generates a driving signal with which the plurality of handpieces is driven. The output switching unit switches the output destinations of the driving signal sent from the driving signal generator so as to select any of the plurality of handpieces. The hand-held members are included in the plurality of handpieces and held for treatments. The hold detecting devices are embedded in the hand-held members, and each detect that the hand-held member is held and produce a predetermined hold detection signal. The output switching control unit receives the hold detection signal and controls the output switching unit that switches the output destinations of the driving signal to select a handpiece from which the hold detection signal is transmitted.

When an operator holds a handpiece the operator wants to use, the output destinations of a driving signal are automatically switched to select the held handpiece. This leads to improved maneuverability for operations.

BRIEF DESCRIPTION OF THE DRAWINGS

FIG. 1 to FIG. 7 are concerned with a first embodiment of the present invention;

FIG. 1 shows an overall configuration of an ultrasonic operation system in accordance with the first embodiment;

FIG. 2 is a block diagram showing the internal configuration of a main apparatus;

FIG. 3 shows the configuration of a hold detecting means;

FIG. 5 is a circuit diagram showing the circuitry of a capacitance sensor circuit included in a hold detecting means;

FIG. 6 is a flowchart describing output port selection;

FIG. 7 shows the configuration of a hold detecting means in accordance with a variant;

FIG. 8 is a perspective view showing the distal end of a scissors-like handpiece;

FIG. 9 shows the overall configuration of an ultrasonic operation system in accordance with the second embodiment of the present invention;

FIG. 10 to FIG. 11C are concerned with a third embodiment of the present invention;

FIG. 10 shows the overall configuration of a surgical operation system in accordance with the third embodiment;

FIG. 11A, FIG. 11B, and FIG. 11C show various types of handpieces;

FIG. 12 shows the major portion of a surgical operation system in accordance with the fourth embodiment;

FIG. 13 shows the configurations of an output switching unit and an extension unit;

FIG. 14 shows the overall configuration of a surgical operation system in accordance with the fifth embodiment;

FIG. 15 is a block diagram showing the internal configuration of a camera control unit;

FIG. 16 shows a monitor on which port information or the like is presented;

FIG. 17 and FIG. 18 are concerned with a sixth embodiment of the present invention;

FIG. 17 shows the overall configuration of a surgical operation system in accordance with the sixth embodiment;

FIG. 18 roughly shows the configuration of a scissors-like handpiece;

FIG. 19 is an explanatory diagram roughly showing the configuration of an ultrasonic operation system in accordance with the seventh embodiment;

FIG. 20 is a block diagram showing the internal configuration of an ultrasonic operation system;

FIG. 21 shows the appearance of a handpiece having a built-in hand switch;

FIG. 22 shows an example of an image displayed on a monitor;

FIG. 23 is a flowchart describing connector selection for an expansion unit;

FIG. 24 is a block diagram showing the configuration of the major portion of a camera control unit employed in the eighth embodiment;

FIG. 25 shows an example of an image displayed on a monitor;

FIG. 26 and FIG. 27 are concerned with a ninth embodiment of the present invention;

FIG. 26 is an explanatory diagram roughly showing the configuration of an ultrasonic operation system in accordance with the ninth embodiment; and FIG. 27 is a circuit block diagram showing the internal configuration of a main apparatus.

Figure 1:
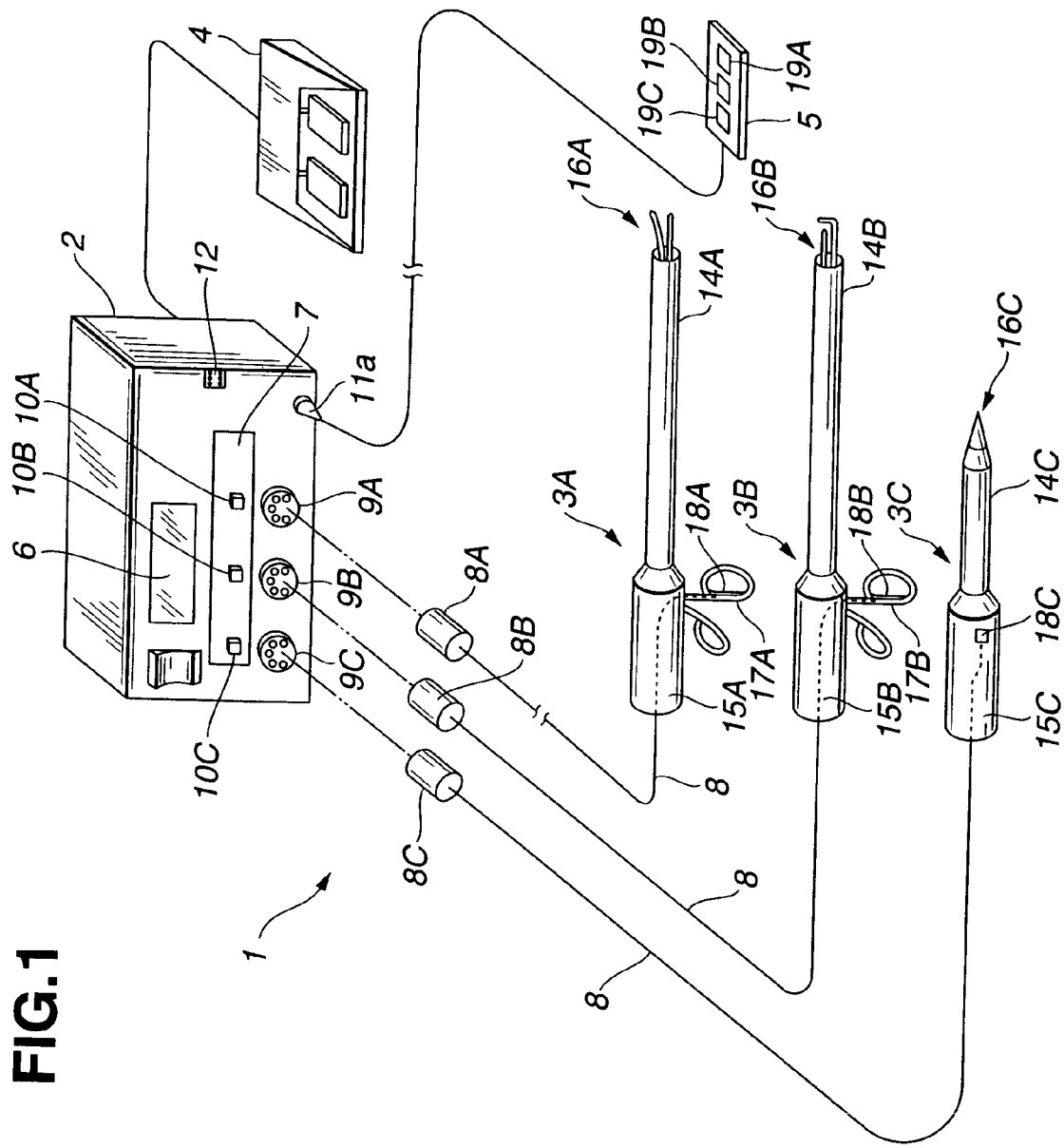

DESCRIPTION OF THE PREFERRED EMBODIMENTS (First Embodiment)

A first embodiment of the present invention will be described with reference to FIG. 1 to FIG. 7.

An ultrasonic operation system 1 in accordance with the first embodiment of the present invention shown in FIG. 1 consists mainly of a main ultrasonic operation apparatus (hereinafter a main apparatus) 2, a plurality of treatment appliances, a footswitch 4, and a remote switch 5. The main apparatus generates a driving signal. The plurality of treatment appliances is connected to the main apparatus 2 so that they can be disconnected freely. The plurality of treatment appliances includes, for example, a scissors-like handpiece 3A, a hook-like handpiece 3B, and a trocar-like handpiece 3C. The footswitch 4 is turned on or off in order to start or stop outputting energy. The remote switch 5 is used for remote control.

According to the present embodiment, the ultrasonic operation system is used to incise or coagulate a lesion using ultrasonic energy. The handpieces 3I (where I denotes A, B, and/or C) has, as described later, an ultrasonic transducer incorporated therein. The main apparatus 2 has an oscillatory circuit incorporated therein so as to apply a driving signal to each ultrasonic transducer.

An operator display panel 6, an operator panel 7, connectors 9A, 9B, and 9C, selection switches 10A, 10B, and 10C, a remote switch connector 11b, and a loudspeaker 12 are exposed on the face of the main apparatus 2. Connector pulses 8A, 8B, and 8C spliced to the ends of cables 8 extending from the scissors-like handpiece 3A, hook-like handpiece 3B, and trocar-like handpiece 3C are joined with the connectors 9A, 9B, and 9C so that they can be disjoined freely. The selection switches 10A, 10B, and 10C are arranged on the operator panel 7 and used to select any connector 9I. A remote switch connector plug 11a (see FIG. 2) attached to a cable extending from the remote switch 5 is joined with the remote switch connector 11b. The loudspeaker 12 is used to inform a result of selection with sound. A foot switch connector 13b (see FIG. 2) with which a footswitch plug 13a attached to a cable extending from the footswitch 4 is exposed on a rear panel on the back of the main apparatus 2.

The handpiece 9I has an elongated sheath 14I and an operator unit (or hand-held member) 15I formed at the back proximal) end of the sheath 14I. An ultrasonic transducer 23 (represented by an ultrasonic transducer incorporated in the scissors-like handpiece 3A in FIG. 2) is incorporated in the operator unit 15I.

The scissors-like handpiece 3A and hook-like handpiece 3B have operator handles 17A and 17B respectively. The operator handle 17A or 17B is manipulated with the fingers of an operator's hand in order to open or close a distal treatment member 16A or 16B for the purpose of an ultrasonic treatment intended for coagulation or any other cure.

In contrast, the trocar-like handpiece 3C has a cylindrical hand-held member 15C thereof directly held by an operator. A distal treatment member 16C of the trocar-like handpiece 3C is used for a treatment.

In the present embodiment, the handpiece 9I has a hold detection sensor 18I that detects (recognizes) whether the handpiece is held.

Specifically, the scissors-like handpiece 3A and hook-like handpiece 3B have sensors 18A and 18B, which serve as hold detecting means for recognizing that the handpieces are held, embedded in the operator handles 17A and 17B respectively. In contrast, the trocar-like handpiece 3C has a sensor 18C disposed on the periphery of the cylindrical operator unit 15C thereof.

When an operator holds the handpiece 9I to be used with his/her hand, the main apparatus 2 detects (recognizes) the hold owing to an output of the sensor 18I. Thus, the handpiece 9I capable of outputting ultrasonic energy can be selected and the footswitch 4 can be stepped on in order to start outputting ultrasonic energy. This results in improved maneuverability.

Moreover, the remote switch 5 includes three selection switches 19A, 19B, and 19C that are used to select the connectors 9A, 9B, and 9C respectively.

Figure 2:
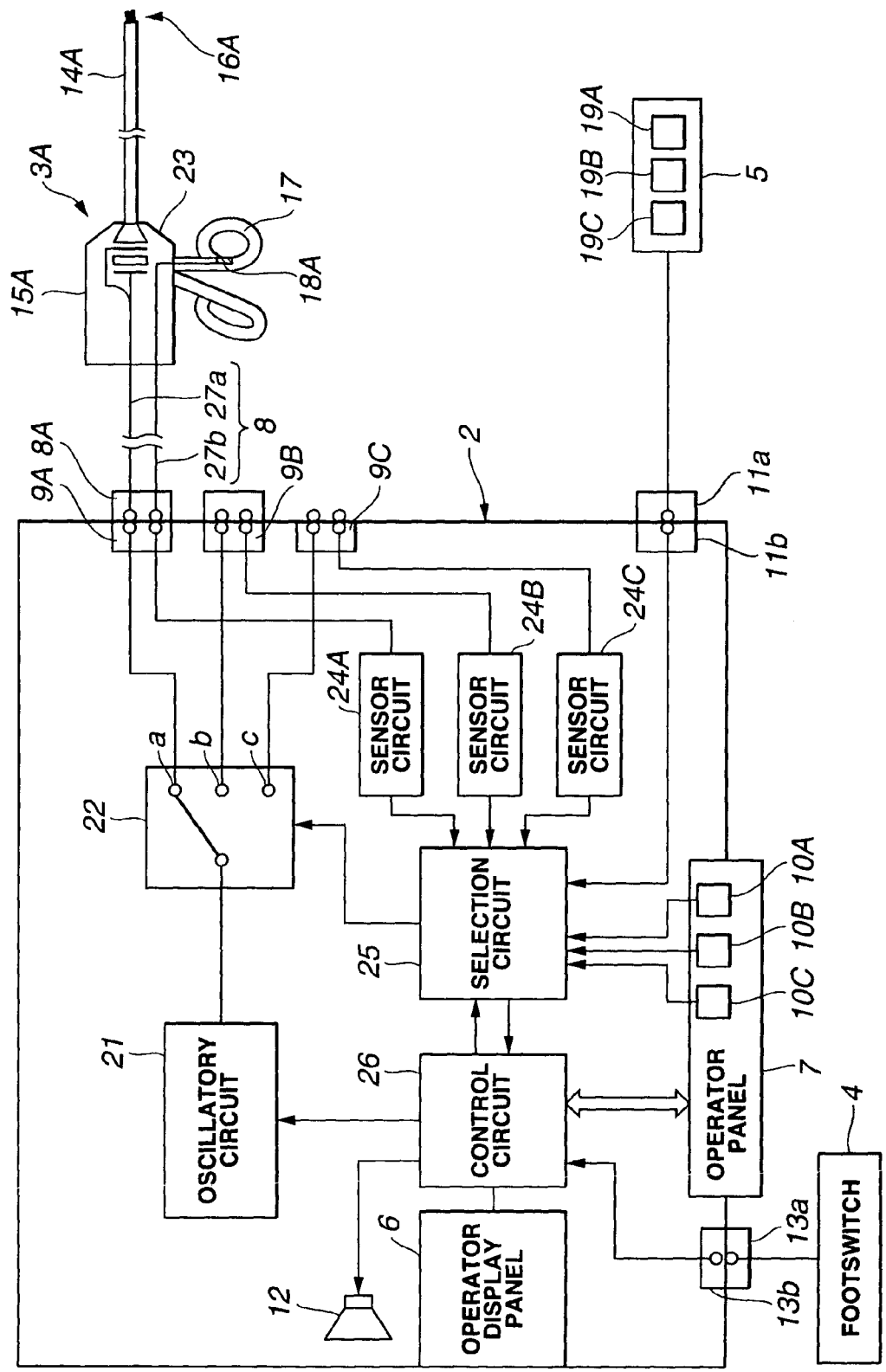

FIG. 2 shows the internal configuration of the main apparatus 2.

The main apparatus 2 includes an oscillatory circuit 21 and a selector switch 22. The oscillatory circuit 21 produces a driving signal with which ultrasonic oscillations are generated. The selector switch 22 serves as a switching means for selectively applying the driving signal, which is produced by the oscillatory circuit 21, to the three connectors 9I (also referred to as output ports).

The driving signal sent from the oscillatory circuit 21 passes through a contact i of the selector switch 22 that is closed, and travels over a driving line 27a contained in the cable 8 through the connector 9I connected to the contact i. The driving signal is then applied to the ultrasonic transducer 23 incorporated in the handpiece 3I. At this time, when an On switch of the footswitch 4 is stepped on, ultrasonic oscillations are generated.

The ultrasonic oscillations are propagated to the distal treatment member 16I over an ultrasound propagation member. When the treatment member 16I is brought into contact with a tissue concerned, the tissue is incised, coagulated, or anyhow treated.

Moreover, a signal detection line 27b coupled to the sensor 18I also runs through the cable 8. A detection signal produced by the sensor 18I is applied to a sensor circuit 24I in the main apparatus 2 by way of the connector plug 8I and connector 9I.

The sensor circuit 24A, 24B, or 24C judges (recognizes) from the output signal of the sensor 18I whether the handpiece 3I is held, and outputs a result of judgment to a selection circuit 25.

Based on the output signal of the sensor circuit 24A, 24B, or 24C, the selection circuit 25 selects the contact i of the selector switch 22 so that the driving signal will be applied to the ultrasonic transducer 23 in the handpiece 3I having the sensor 18I that has judged that the handpiece is held.

A selection signal induced with a press of the selection switch 10I exposed on the operator panel 7 and a selection signal induced with a press of the selection switch 19I included in the remote switch 5 are also applied to the selection circuit 25. When an operator presses any of the selection switches 10I and 19I, the connections of the oscillatory circuit 21 via the selector switch 22 are switched so that the contact i whose selection is instructed will be closed. Consequently, a driving signal can be output to the ultrasonic transducer 23 in the handpiece 3I connected to the closed contact i.

A control circuit 26 responsible for control of the whole apparatus is incorporated in the main apparatus 2. For example, when the footswitch 4 is stepped on, a signal induced with the stepping is transferred to the control circuit 26. The control circuit 26 controls the oscillatory circuit 21 to start or stop oscillation (or in other words, start or stop outputting oscillatory energy).

Moreover, when the operator panel 7 is used to set an energy level, the control circuit 26 controls output of oscillations produced by the oscillatory circuit 21 according to the set value.

When the contacts i of the selector switch 22 are switched based on a signal sent from the selection circuit 25, information indicating which of the contacts i is closed is communicated from the selection circuit 25 to the control circuit 26. The control circuit 26 in turn visually indicates the information or the connector 9I (or port number) connected to the closed contact i using the operator display panel 6. Alternatively, the control circuit 26 audibly notifies the information or the connector using the loudspeaker 12.

Figure 3:
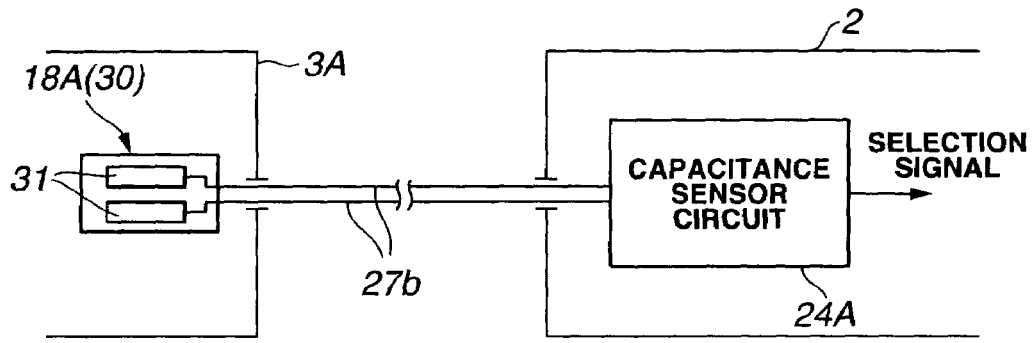

Next, the sensor 18A (18B or 18C) serving as a hold detecting means will be described with reference to FIG. 3.

A hold detecting method adopted herein is based on judgment from a change in electrostatic capacitance.

A sensing device 30 included in the sensor 18A consists of two metallic electrodes 31 juxtaposed on an insulating plate. The sensing device 30 is electrically connected to the capacitance sensor circuit 24A included in the main apparatus 2 over signal lines 27b extending from the two electrodes 31.

When an operator's hand is placed over the two electrodes 31, an electrostatic capacitance offered by the two electrodes 31 changes. The capacitance sensor circuit 24A detects (recognizes) the change, and produces a selection signal. Accordingly, the contacts i of the selector switch 22 are switched.

Figure 4A:
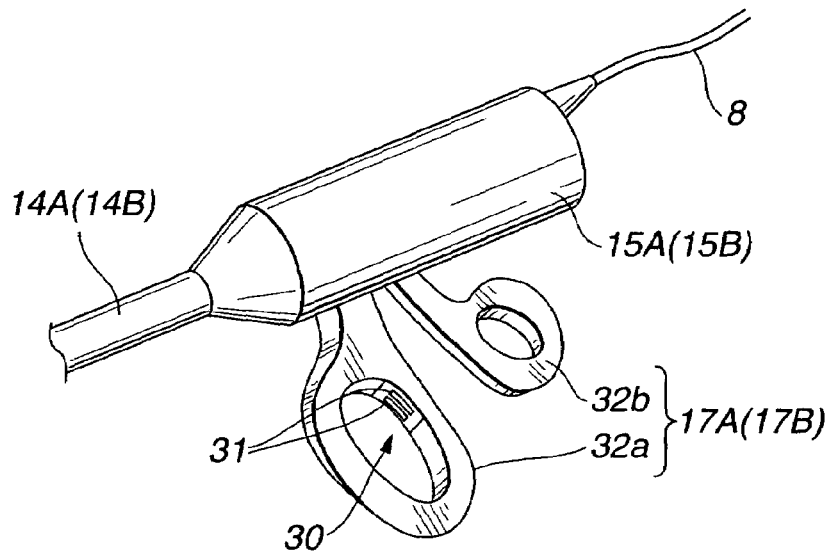
FIG. 4A and FIG. 4B are perspective views showing handpieces including hold detection sensors.

When a handpiece has a handle like the one shown in FIG. 4A (handpiece 3A or 3B), the sensing device 30 composed of the two electrodes 31 should be embedded in an inner wall of a stationary handle 32a of the operator handle 17A or 17B or of a movable handle 32b thereof.

Figure 4B:
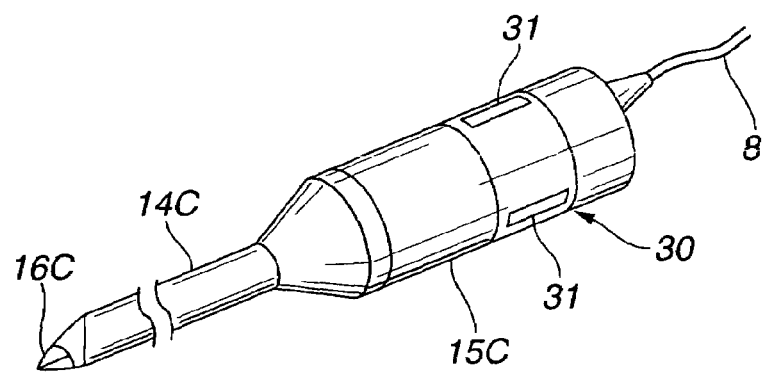

When a handpiece employed is the trocar-like handpiece 3C like the one shown in FIG. 4B, the two electrodes 31 should be disposed at, for example, upper and lower points on the hand-held member 15C of the handpiece. In this case, incorrect sensing can be avoided. Namely, when the handpiece 3C is, for example, placed by the side of a patient, although an operator does not hold the handpiece 3C, an electrostatic capacitance changes. Consequently, it may be incorrectly sensed that the handpiece 3C is held.

Figure 5:
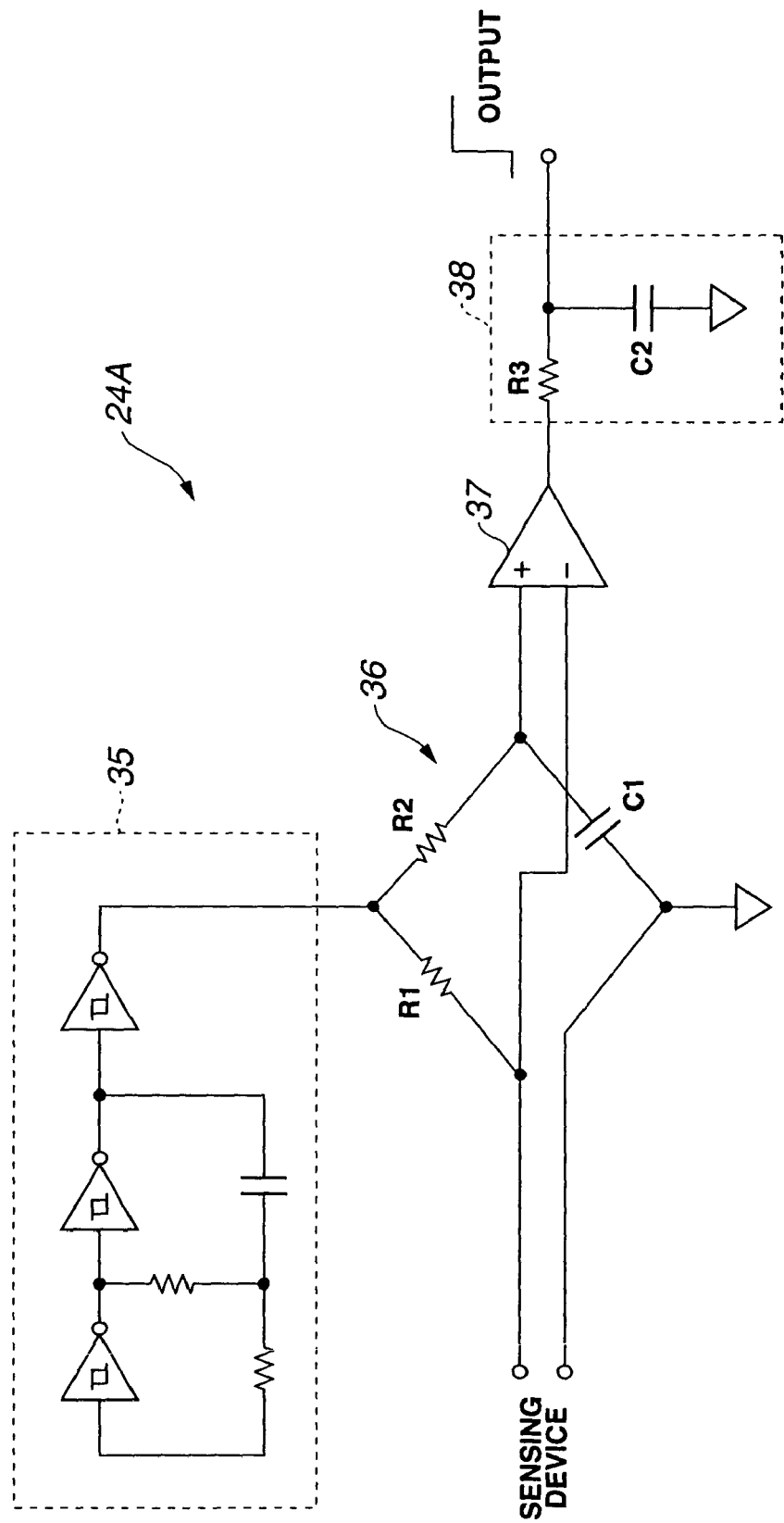

Next, an example of circuitry of the capacitance sensor circuit 24A (or 25B or 24C) will be described with reference to FIG. 5.

The capacitance sensor circuit 24A consists mainly of an oscillatory circuit 35, a Wheatstone bridge 36, a comparator 37, and a filter 38. An oscillatory signal sent from the oscillatory circuit 35 is applied to the Wheatstone bridge 36, and the sensing device 30 is connected to the Wheatstone bridge 36. The comparator 37 judges a state sensed by the sensing device 30 from an output signal of the Wheatstone bridge 36. The filter 38 provides a binary-coded signal associated with the sensed state according to an output of the comparator 37.

The oscillatory circuit 35 includes, for example, an inverter (realized with a Schmitt circuit) and produces a signal whose frequency ranges from several kilohertz to several hundred kilohertz. An oscillatory output of the oscillatory circuit 35 is applied to the Wheatstone bridge 36 having four impedance devices including the sensing device 30 connected in the form of a bridge. More particularly, the oscillatory output is applied to a node between resistors R1 and R2 and to a node between a capacitor C1 and one terminal of the sensing device 30.

A signal used to detect a potential at a node between the resistor R1 and the other terminal of the sensing device 30 and a signal used to detect a potential at a node between the resistor R1 and the capacitor C1 are applied to the input terminals of the comparator 37. It is thus detected whether the potentials are balanced.

To be more specific, one of four impedance devices constituting the Wheatstone bridge 36 is replaced with the sensing device 30 composed of the two electrodes 31 and included in the handpiece 3I. Consequently, a change in a capacitive component can be detected as a change dependent on whether an operator's hand is placed over the two electrodes 31. Eventually, it can be recognized that an operator holds the handpiece 3I.

For example, when the sensing device 30 is not held, a capacitance offered by the electrodes is small and an impedance offered thereby is high. The potential at the sensing device 30 is therefore higher than the potential at the capacitor C1. An output of the comparator is therefore driven low.

When the sensing device 30 is held and the electrostatic capacitance is large, the potential at the sensing device 30 is lower than the potential at the capacitor C1. The output of the comparator is therefore driven high. The capacitance of the capacitor C1 or the resistances of the resistors R1 and R2 are determined to meet the above conditions.

In this case, an output of the sensing device is modulated with an oscillatory output (alternating output), and passed through the filter 38. The filter 38 has the capability of a low-pass filter to pass a component whose frequency is lower than an oscillating frequency at which the oscillatory output is provided, and consists of a resistor R3 and a capacitor C2. Consequently, an output signal of the filter 38 makes a low-to-high transition along with a change of the state of the handpiece into a held state.

As mentioned above, according to the present embodiment, the connector plug 8I attached to the cable extending from the handpiece 3I is joined with the connector 9I formed on the main apparatus 2. When an operator presses the selection switch 10I on the operator panel 7 or the selection switch 19I included in the remote switch 5, the handpiece 3I the operator wants to use is selected. When outputting energy is started with a step on the footswitch 4, an operation can be performed. The handpiece 3I has the sensor 18I for detecting a hold embedded in its portion to be held by an operator. In the main apparatus 2, an output signal of the sensor 18I is checked, and the contacts i of the selector switch 22 are automatically switched so that an ultrasonic driving signal will be applied to the held handpiece 3I. Consequently, an operation can be performed.

Operations to be exerted by the present embodiment having the foregoing components will be described with reference to FIG. 6. As shown in FIG. 1, one handpiece 3I or a plurality of handpieces 3I including the scissors-like handpiece 3A is connected to the main apparatus 2 for treatment.

For example, the handpiece 3A is, as shown in FIG. 2, connected to the main apparatus 2. When the operator handle 17A of the handpiece 3A is held, a detection signal associated with the held state is sent from the sensor 18A to the sensor circuit 24A.

Based on the detection signal, the sensor circuit 24A sends a selection signal, which indicates that the handpiece 3A is held, to the selection circuit 25. The selection circuit 25 judges that the selection signal has been sent from the sensor circuit 24A out of the plurality of sensor circuits 24A, 24B, and 24C.

Consequently, the selection circuit 25 sends a switching control signal to the selector switch 22 so that an output line extending from the oscillatory circuit 21 will be routed to the connector 9A connected to the held handpiece 3A, or in other words, a contact a will be selected. A result of selection performed by the selection circuit 25 is communicated to the control circuit 26, and presented on the operator display panel 6 and/or notified using the loudspeaker 12.

As mentioned above, when the handpiece 3A or the like is held actually, the connections of the oscillatory circuit 21 via the selector switch 22 are automatically switched based on an output signal of the sensor circuit 24A. Alternatively, the selection circuit 25 may make a judgment from whether the selection switch 10I on the operator panel 7 or the selection switch 19I included in the remote switch 5 is pressed. Based on a result of judgment, the selector switch 22 may be acted to select any of the connections.

Actions to be performed in the main apparatus have been described briefly. Selecting any of the output ports (connectors 9I) on the main apparatus 2 is performed as described in FIG. 6.

The selection circuit 25 judges at step S1 in FIG. 6 whether any of the selection switches 10A to 10C on the operator panel 7 has been pressed. If no selection switch is pressed, it is judged at step S2 whether any of the selection switches 19A to 19C included in the remote switch 5 has been pressed. If no selection switch is pressed, it is judged at step S3 whether a selection signal has been received from any of the sensor circuits 24A to 24C. If no selection signal is received, control is returned to step S1.

If the judgment at any of steps S1 to S3 is made in the affirmative, control is passed to step S4. Control is then given to select any of the contacts i of the selector switch 22 according to a selection signal induced with a press of any of the selection switches 10A to 10C on the operator panel 7 or the selection switches 19A to 19C included in the remote switch 5, or a selection signal sent from any of the sensor circuits 24A to 24C. Consequently, a driving signal will be applied through the output port (any of connectors 9A to 9C) connected to the selected contact.

For example, if it is judged at step S1 that the selection switch 10A on the operator panel 7 has been pressed, a signal induced with the press is transferred to the selection circuit 25. The selection circuit 25 performs a selecting (switching) action to close the contact a of the selector switch 22.

If none of the selection switches 10A to 10C on the operator panel 7 is pressed and the selection switch 19A included in the remote switch 5 has been pressed, a signal induced with the press is transferred to the selection circuit 25. The selection circuit 25 performs an action of selecting any of the contacts of the selector switch 22.

None of the switches 10A to 10C and 19A to 19C may be pressed, but a signal indicating that the handpiece 3I has been selected may be transferred to the selection circuit 25 owing to any of the sensors 18A to 18C, which are included in the handpieces 3I and serve as hold recognizing means, and the sensor circuits 24A to 24C incorporated in the main apparatus 2. In this case, any of the contacts of the selector switch 22 is selected based on the signal.

Moreover, when an output port is selected, the selected output port is informed an operator by means of a sound generated from the loudspeaker 12 or using a display means that is the operator display panel 6. Control is then returned to step S1.

As mentioned above, a hold detecting means can be constructed merely by including two electrodes in a handpiece. The selection switch 10I on the operator panel 7 or the selection switch 19I included in the remote switch 5 need not be pressed. Nevertheless, whichever of the handpieces 3I an operator holds can be automatically recognized, and the operator can use the held handpiece. This leads to drastically improved maneuverability.

In the aforesaid embodiment, the sensor 18I and capacitance sensor circuit 24I are used as a hold detecting means. Alternatively, as shown in FIG. 7, an infrared sensor 39 may be adopted as the sensing device 30 serving as the sensor 18I included in the handpiece 3I, and an infrared sensor circuit 40 may be incorporated in the main apparatus 2.

The infrared sensor 39 consists mainly of an infrared emitting device and an infrared detecting device (infrared detection phototransistor or photodiode). The infrared emitting device emits infrared light. The infrared detecting device detects infrared light emitted from the infrared emitting device. Herein, an amount of infrared light received by the infrared detecting device varies largely depending on whether a handpiece is held.

An output signal of the infrared detecting device is sent to the infrared sensor circuit 40. The infrared sensor circuit 40 judges whether the handpiece is held.

A result of selecting an output port may be notified by voice composed within the main apparatus 2.

The present embodiment has advantages described below.

When it is detected based on an output of the hold detection sensor 18I embedded in the handpiece 3I that the handpiece 3I is actually held, the handpiece is automatically selected so that the handpiece can output treatment energy. Once the handpiece 3I is held, an operator can use the handpiece 3I for treatment but need not change handpieces. This leads to improved user friendliness, that is, greatly improved maneuverability.

Moreover, treatment will not be suspended because handpieces need not be changed. Treatment can be achieved smoothly.

(Second Embodiment)

Figure 8:
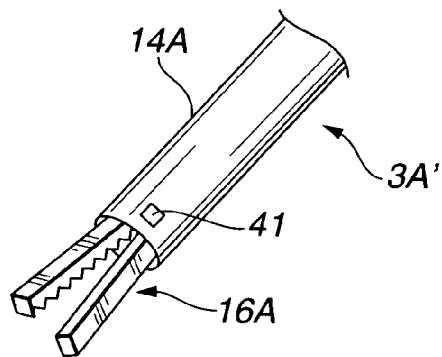
FIG. 8 and FIG. 9 are concerned with a second embodiment of the present invention.

Next, the second embodiment of the present invention will be described with reference to FIG. 8 and FIG. 9. FIG. 8 shows the distal part of a scissors-like handpiece 3A'. In the present embodiment, an LED 41A is disposed near the treatment member 16A projecting from the tip of a sheath 14A.

To be more specific, the scissors-like handpiece 3A' is different from the scissors-like handpiece 3A described in relation to the first embodiment in a point that the LED 41A is disposed near the treatment member 16A projecting from the tip of the sheath 14A. Moreover, a hook-like handpiece 3B' shown in FIG. 9 has an LED 41B disposed near the treatment member 16B thereof.

Figure 9:
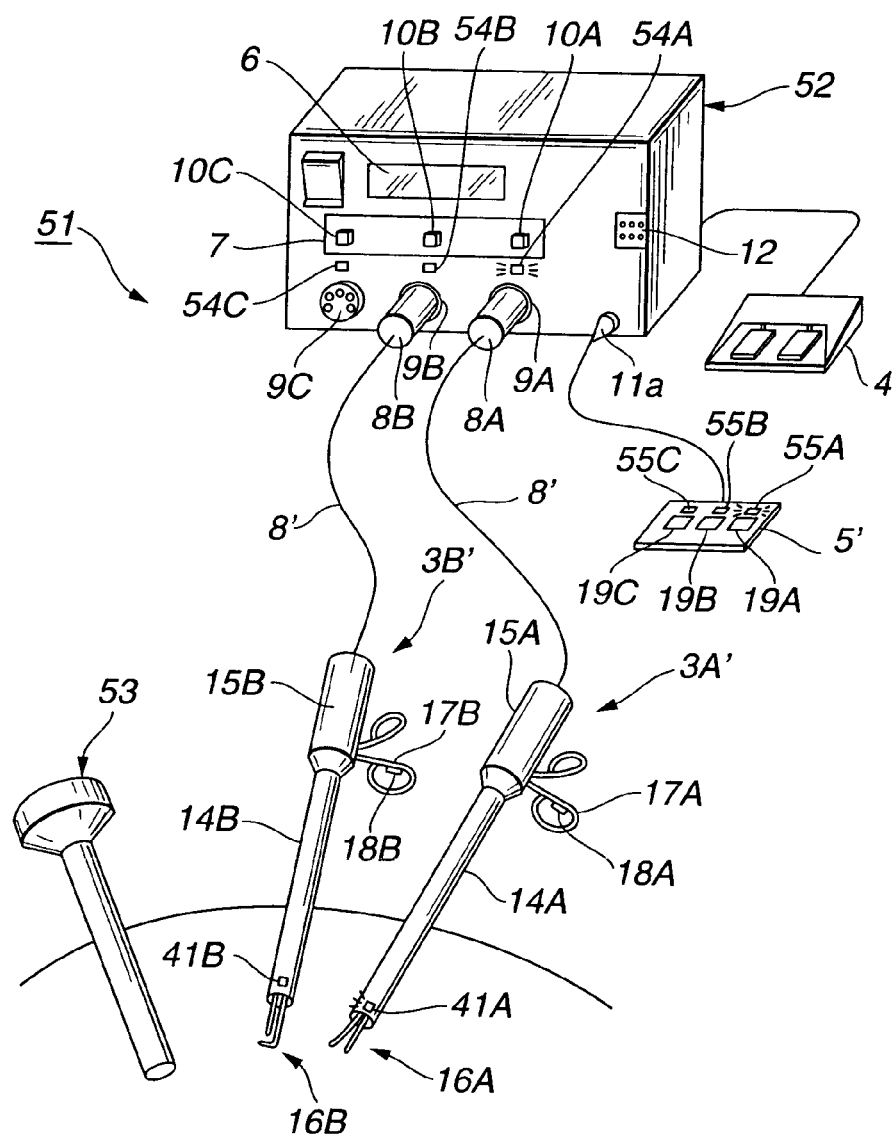

FIG. 9 is an explanatory diagram concerning the overall configuration of an ultrasonic operation system 51 in accordance with the second embodiment. The ultrasonic operation system 51 consists mainly of a main apparatus 52, handpieces 3A' and 3B', the footswitch 4, a remote switch 5', and an endoscope 53 used to observe a region to be operated on.

The main apparatus 52 included in the present embodiment is different from the main apparatus 2 included in the first embodiment in a point that LEDs 54A to 54C are disposed near the selection switches 10A to 10C located on the operator panel 7.

Moreover, according to the present embodiment, a cable 8' is different from the cable 8 included in the first embodiment in a point that the cable 8' contains a signal line coupled to the LED 41I. The cable 8' is routed to the control circuit 26 (see FIG. 2) included in the main apparatus 52 by way of the connector plug 8I and connector 9I.

Moreover, the remote switch 5' included in the present embodiment is different from the remote switch 5 included in the first embodiment in a point that LEDs 55I are disposed near the selection switches 19I.

The other components are identical to those of the first embodiment. The same reference numerals will be assigned to components identical to those of the first embodiment, and the description of the components will be omitted.

Next, operations to be exerted by the present embodiment will be described below.

One of the plurality of handpieces 3A' and 3B' is selected owing to the remote switch 5' and the hold detecting means employed even in the first embodiment. When the handpiece 3I' to be used is selected, for example, when the scissors-like handpiece 3A is selected, the LED 41A disposed near the distal end of the handpiece 3A emits light. Therefore, an operator readily identifies the handpiece 3A' that can output energy while treating a lesion under observation through the endoscope 53.

Moreover, the LED 55I disposed near the selection switch 19I included in the remote switch 5' emits light, and the LED 54I disposed near the selection switch 10I located on the operator panel 7 of the main apparatus 52 emits light. Thus, a result of selection is notified.

According to the present embodiment, even when an operator is performing an operation using the endoscope 53, the operator can identify the selected handpiece 31' without being distracted from an image produced by the endoscope 53. This leads to improved maneuverability. The present embodiment provides the same advantages as the first embodiment does.

(Third Embodiment)

Next, a third embodiment of the present invention will be described with reference to FIG. 10 to FIG. 11C.

Figure 10:
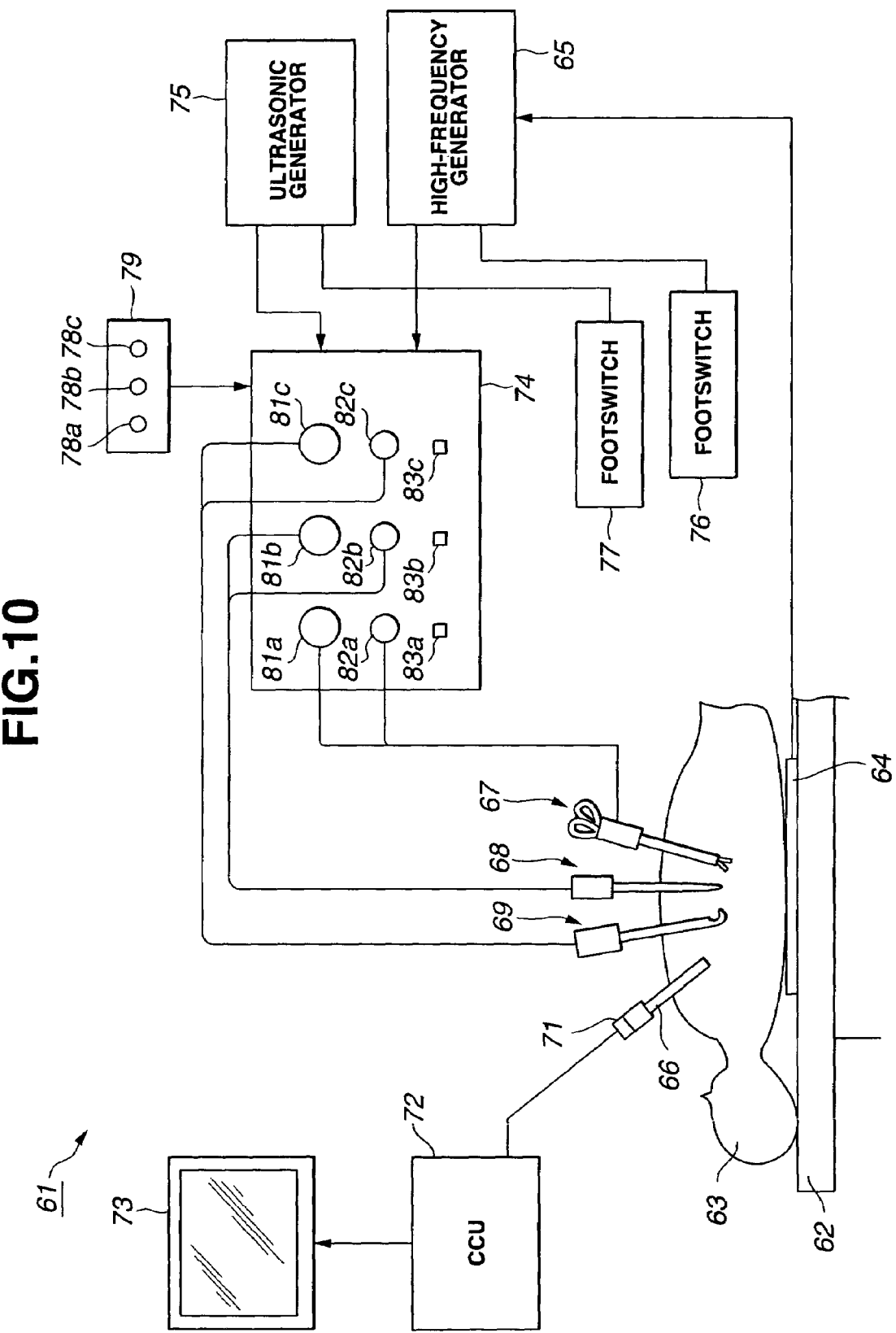

As shown in FIG. 10, in a (endoscopic) high-frequency/ultrasonic surgical operation system 61 in accordance with the third embodiment of the present invention, a counter electrode plate 64 is interposed between an operating table 62 and a patient 63 lying down on the operating table 62.

An electrode on the counter electrode plate 64 is connected to a high-frequency generator 65 over a cable. A rigid endoscope 66, a scissors-like handpiece 67, a rod-like handpiece 68, and a hook-like handpiece 69 are inserted into the abdomen of the patient 63 over a sheath that is not shown.

A TV camera head 71 with a built-in imaging device is mounted on the back end of the rigid endoscope 66. The TV camera 71 is connected to a camera control unit (hereinafter CCU) 72, and processes a signal produced by the imaging device. A standard video signal produced by the CCU 72 is transferred to a TV monitor 73. An endoscopic image picked up by the imaging device is displayed on the display screen of the TV monitor 73.

The scissors-like handpiece 67, rod-like handpiece 68, and hook-like handpiece 69 are connected to the high-frequency generator 65 and an ultrasonic generator 75 via an output switching unit 74 for switching routes of an output line extending from each of the generators.

The high-frequency generator 65 and ultrasonic generator 75 are connected to footswitches 76 and 77 respectively which are turned on or off in order to start or stop outputting high-frequency or ultrasonic energy.

Moreover, the output switching unit 74 has, for example, three ports a, b, and c. A hand-held switch 79 including a port a selection switch 78a, a port b selection switch 78b, and a port c selection switch 78c used to select the ports a, b, and c respectively is connected to the output switching unit 74.

An ultrasonic connector attached to a cable extending from the scissors-like handpiece 67 is joined with an ultrasound output connector 81a formed on the output switching unit 74. An active-cord mechanism contained in the cable is coupled to a high-frequency output connector 82a.

An ultrasonic connector attached to a cable extending from the rod-like handpiece 68 is joined with an ultrasound output connector 81b formed on the output switching unit 74. An active-cord mechanism contained in the cable is coupled to a high-frequency output connector 82b. An ultrasonic connector attached to a cable extending from the hook-like handpiece 69 is joined with an ultrasound output connector 81c formed on the output switching unit 74. An active-cord mechanism contained in the cable is coupled to a high-frequency output connector 82c.

The output switching unit 74 has a port a selection indictor 83a, a port b selection indicator 83b, and a port c selection indictor 83c.

Figure 11A:
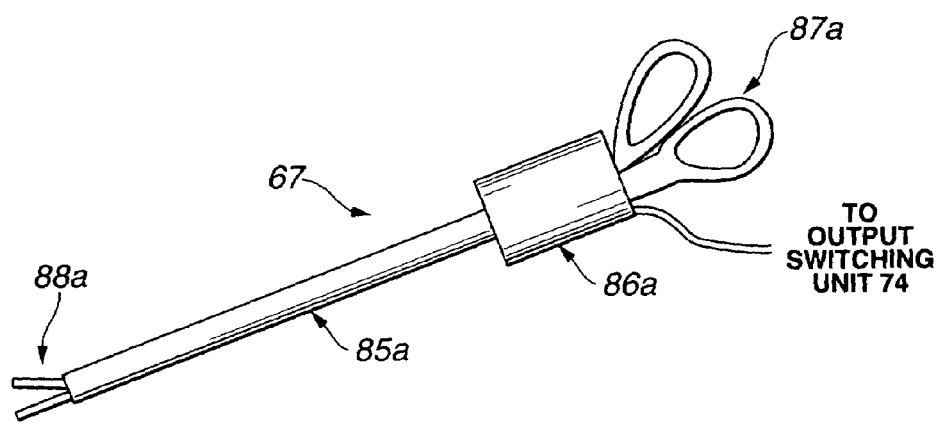

As shown in FIG. 11A, the scissors-like handpiece 67 consists mainly of a probe 85a and a transducer 86a attached to the back end of the probe 85a. A handle 87a is disposed at the back end of the transducer 86a. The handle 87a is manipulated in order to turn a movable piece of a clamping member 88a projecting from the tip of the probe and thus clamp a lesion to be treated.

Figure 11B:
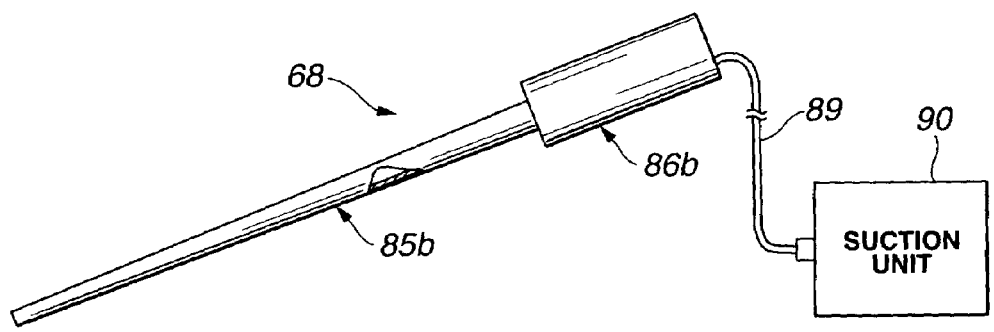

The rod-line handpiece 68 consists of, as shown in FIG. 11B, a probe 85a and a transducer 86b. The probe 85b is hollowed, and the hollow is connected to a suction unit 90 by way of a suction tube 89.

Figure 11C:
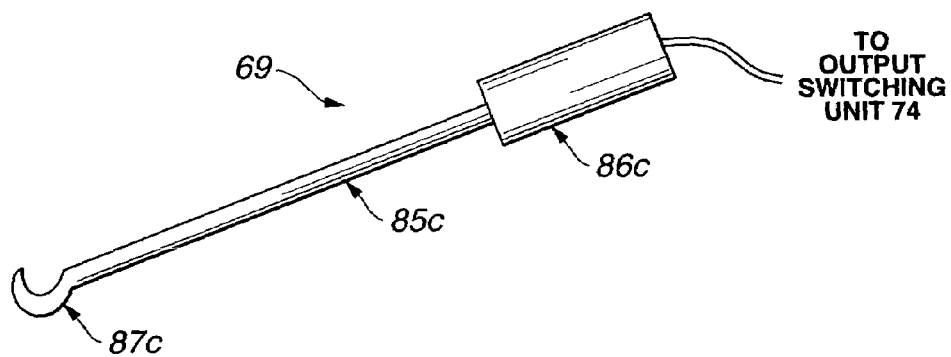

The hook-like handpiece 69 consists of, as shown in FIG. 11C, a probe 85c and a transducer 86c. A hook 87c is formed as the distal part of the probe 85c.

Next, operations to be exerted by the present embodiment will be described below.

With the rigid endoscope 66, scissors-like handpiece 67, rod-like handpiece 68, and hook-like handpiece 69 inserted in the body of the patient 63, an operator observes the distal parts of the handpieces by viewing an image produced by the rigid endoscope 66. In other words, a view image picked up by the rigid endoscope 66 is converted into an electrical signal by the TV camera head 71. The electrical signal is then converted into a standard video signal by the CCU 72. Consequently, the view image is displayed on the TV monitor 73.

While viewing the image on the TV monitor 73, the operator moves the scissors-like handpiece 67 out of the handpieces 67 to 69 to a desired position in a region to be operated on. The operator presses the port c selection switch 78c included in the hand-held switch 79 so as to set an energy output port to the port c of the output switching unit 74.

The state that the port c has been selected is indicated by the port c selection indicator 83c on the output switching unit 74. Supposing the peritoneum of the patient 63 is incised in an early stage of an operation, the operator uses the hook-like handpiece 69 to hook the peritoneum with the hook 87c, and then steps on the footswitch 76.

A signal induced with the stepping of the footswitch 76 is transferred to the high-frequency generator 65, whereby high-frequency energy is fed to a high-frequency input connector, which is not shown, on the output switching unit 74. Since the port c selection switch 78c has been selected, the high-frequency energy fed to the high-frequency input connector is transferred to the probe 85c through the high-frequency output connector 82c. The high-frequency energy flows into the counter electrode plate 64 through the peritoneum, and returns to the high-frequency generator 65. The peritoneum is incised with the high-frequency energy passing through the peritoneum.

When the energy level may be low, an operator steps on the footswitch 77. A signal induced with the stepping of the footswitch 77 is transferred to the ultrasonic generator 75. Ultrasonic energy is then fed to an ultrasound input connector, which is not shown, on the output switching unit 74. Since the port c selection switch 78c has been selected, the ultrasonic energy fed to the ultrasound input connector is transferred to the probe 85c through the ultrasound output connector 81c. Eventually, the peritoneum is incised.

In short, an operator can switch the incising energies to be output from the hook-like handpiece 69 merely by changing the footswitches 77 and 76 to be stepped on. When an operation progresses, a vessel may have to be treated. In this case, the operator presses the port a selection switch 78a included in the hand-held switch 79 so as to set an energy output port to the port a of the output switching unit 74.

In this case, the port c selection indicator 83c is put out, and the port a selection indicator 83a is lit. The operator manipulates the handle 87a of the scissors-like handpiece 67 to clamp a vessel with the clamping member 88a. The operator then steps on the footswitch 77, whereby a signal induced with the stepping of the footswitch 77 is transferred to the ultrasonic generator 75. Ultrasonic energy is fed to the ultrasound input connector, which is not shown, on the output switching unit 74.

Since the output port a has been selected, the ultrasonic energy fed to the ultrasound input connector is propagated to the clamping member 88a of the scissors-like handpiece 67 through the ultrasound output connector 88a. Consequently, the vessel clamped by the clamping member 88a is cut while being coagulated.

Moreover, if the necessity of incising any other tissue arises during the above treatment, the operator steps on the footswitch 76 while pressing the distal part of the scissors-like handpiece 67 against the tissue to be incised. Consequently, high-frequency energy is propagated from the high-frequency generator 75 to the clamping member 88a of the scissors-like handpiece 67. The tissue in contact with the clamping member 88a is thus incised.

If the operator finds a malignant tissue and wants to remove the tissue, the operator presses the port b selection switch 78b included in the hand-held switch 79. Consequently, the port b of the output switching unit 74 is set as an energy output port. In this case, the operator steps on the footswitch 77 with the distal part of the rod-like handpiece 68 pressed against the malignant tissue. Consequently, ultrasonic energy is propagated from the ultrasonic generator 75 to the probe 85b. Eventually, the malignant tissue is destroyed and emulsified.

The suction unit 90 is connected to the probe 85b by way of the suction tube 89. The emulsified malignant tissue is sucked by the suction unit 90 by way of the suction tube 89 and removed from the region to be operated on. At this time, if any peripheral tissue hemorrhages, the operator brings the distal part of the probe 85b into contact with the hemorrhaging tissue, and steps on the footswitch 76. Consequently, high-frequency energy is propagated to the probe 85b, whereby the hemorrhage is arrested.

The present embodiment provides the advantage described below.

According to the present embodiment, if various treatments are given during one operation, a probe whose shape is optimal for each treatment can be readily selected and used. This leads to a great reduction in an operating time.

(Fourth Embodiment)

Next, a fourth embodiment of the present invention will be described with reference to FIG. 12 and FIG. 13. The same reference numerals will be assigned to components identical to those of the third embodiment, and the description of the components will be omitted.

Figure 12:
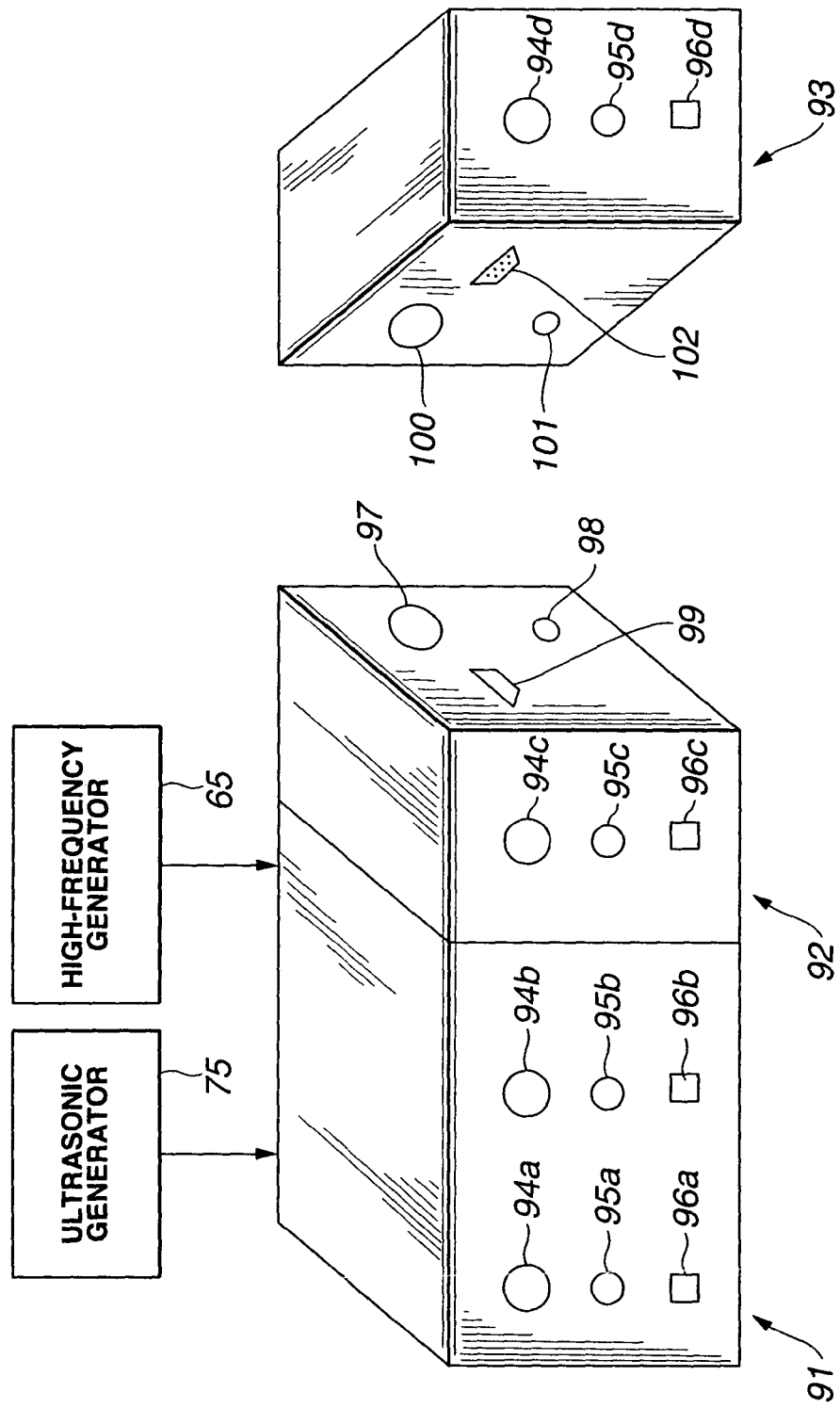
FIG. 12 and FIG. 13 are concerned with a fourth embodiment of the present invention.

As shown in FIG. 12, a (first) extension unit 92 can be freely detachably attached to a main output switching unit 91. A (second) extension unit 93 can be freely detachably attached to the extension unit 92. In FIG. 12 and FIG. 13, the extension unit 92 is attached to the main output switching unit 91.

The main output switching unit 91 has a port a ultrasound output connector 94a, a port a high-frequency output connector 95a, a port a selection switch 96a, a port b ultrasound output connector 94a, a port b high-frequency output connector 95b, and a port b selection switch 96b arranged on an operator panel thereof.

Figure 13:
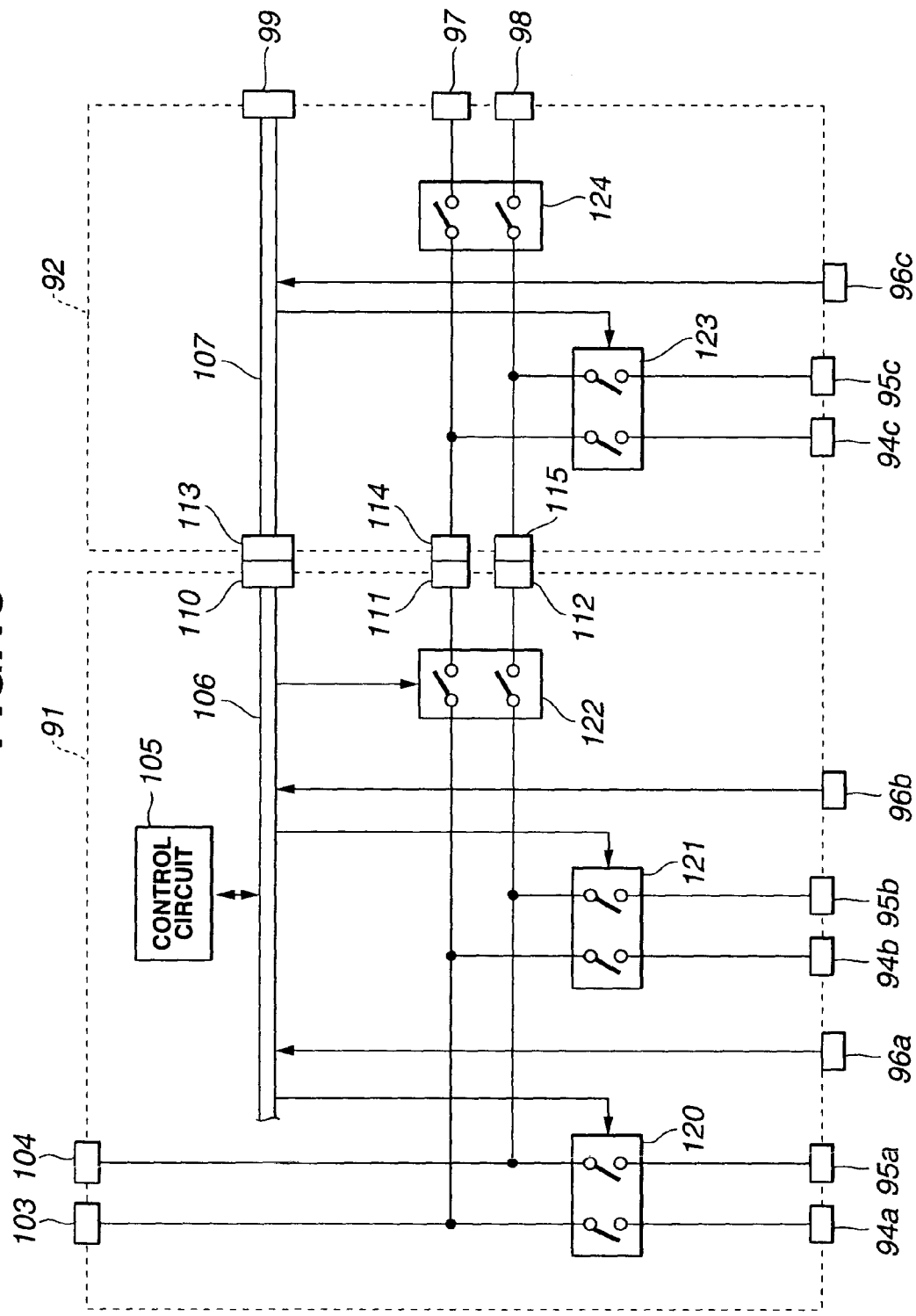

As shown in FIG. 13, an ultrasonic joint plug 111, a high-frequency joint plug 112, and a control plug 110 are formed on the right side surface of the main output switching unit 91.

As shown in FIG. 12 and FIG. 13, the extension unit 92 has a port c ultrasound output connector 94c, a port c high-frequency output connector 95c, and a port c selection switch 96c arranged on the front panel thereof.

The extension unit 93 has a port d ultrasound output connector 94d, a port d high-frequency output connector 95d, and a port d selection switch 96d arranged on the front panel thereof.

As shown in FIG. 13, an ultrasonic joint connector 114, a high-frequency joint connector 115, and a control connector 113 are formed on the left side surface of the extension unit 92. The output switching unit 91 and extension unit 92 are freely detachably attached to each other using an attaching/detaching mechanism that is not shown. At this time, the output switching unit 91 and extension unit 92 are juxtaposed so that the ultrasonic joint plug 111 will be automatically joined with the ultrasonic joint connector 114, the high-frequency joint plug 112 will be automatically joined with the high-frequency joint connector 115, and the control plug 110 will be automatically joined with the control connector 113.

Moreover, an ultrasonic joint plug 97, a high-frequency joint plug 98, and a control plug 99 are arranged on the right side surface of the extension unit 92. The ultrasonic joint plug 97, high-frequency joint plug 98, and control plug 99 are joined with an ultrasonic joint connector 100, a high-frequency joint connector 101, and a control connector 102 formed on the extension unit 93 that has the same structure as the extension unit 92 as shown in FIG. 12.

As shown in FIG. 13, the ultrasonic generator 75 is connected to the main output switching unit 91 through an ultrasound input connector 103. The high-frequency generator 65 is connected thereto through a high-frequency input connector 104.

The ultrasound input connector 103 is connected to a port a switching relay 120, a port b switching relay 121, and an extension unit relay 122. The high-frequency input connector 104 is connected to the port a switching relay 120, port b switching relay 121, and extension unit relay 122. The port a switching relay 120 is connected to the port a ultrasound output connector 94a and port a high-frequency output connector 95a.

The port b switching relay 121 is connected to the port b ultrasound output connector 94b and port b high-frequency output connector 95b. The extension unit relay 122 is connected to the ultrasonic joint plug 111 and high-frequency joint plug 112. A control circuit 105 is incorporated in the main output switching unit 91, and connected on a control bus 106.

Control lines extending from the port a switching relay 120, port b switching relay 121, and extension unit relay 122 are routed to the control bus 106. The port a selection switch 96a and port b selection switch 96b located on the front panel are connected on the control bus 106. The control bus 106 is routed to the control plug 110.

A control bus 107 is routed to the control connector 113 formed on the extension unit 92. A port c switching relay 123 and an extension unit relay 124 are incorporated in the extension unit 92. The ultrasound joint connector 114 is connected to the port c switching relay 123 and extension unit relay 124. The high-frequency joint connector 115 is connected to the port c switching relay 123 and extension unit relay 124.

The relay 123 is connected to the port c ultrasound output connector 94c and port c high-frequency output connector 95c. The extension unit relay 124 is connected to the ultrasound joint plug 97 and high-frequency joint plug 98.

Control lines extending from the port c switching relay 123 and extension unit relay 124 are routed to the control bus 107. The port c selection switch 96c and control plug 99 are connected on the control bus 107.

Next, operations to be exerted by the present embodiment will be described below.

When three handpieces are employed in the same manner as they are in the third embodiment, the extension unit 92 is attached to the output switching unit 91. Consequently, the ultrasound joint plug 111 is joined with the ultrasound joint connector 114, the high-frequency joint plug 112 is joined with the high-frequency connector 115, and the control plug 110 is joined with the control connector 113.

When the control plug 110 and control connector 113 are joined, information of the joint is communicated to the control circuit 105. The control circuit 105 closes the extension unit relay 122. On the other hand, nothing is joined with the control plug 99. The control circuit 105 keeps the extension unit relay 124 open.

The scissors-like handpiece 67 is plugged in to the port a, the rod-like handpiece 68 is plugged in to the port b, and the hook-like handpiece 69 is plugged in to the port c.

When an operator wants to treat a vessel using the scissors-like handpiece 67, the operator presses the port a selection switch 96a on the output switching unit 91. A signal induced with the press of the port a selection switch 96a is transferred to the control circuit 105. The control circuit 105 closes the port a switching relay 120. Consequently, ultrasonic energy and high-frequency energy can be propagated to the scissors-like handpiece through the port a.

When an operator wants to resect a malignant tissue using the rod-like handpiece 68, the operator presses the port b selection switch 96b on the output switching unit 91. A signal induced with the press of the port b selection switch 96b is transferred to the control circuit 105. The control circuit 105 opens the port a switching relay 120 and closes the port b switching relay 121. Consequently, ultrasonic energy and high-frequency energy can be propagated to the rod-like handpiece 68 through the port b. The same applies to a case where the port c is selected.

When an operator intends to use only two types of handpieces, the operator detaches the extension unit 92 from the output switching unit 91. When the control plug 110 and control connector 113 are disjoined, the control circuit 105 opens the extension unit relay 122. Consequently, the operator performs an operation with any handpieces plugged in to the port a and port b.

A plurality of extension units may be attached to the extension unit 92. Operations to be exerted in this case are nearly identical to the aforesaid ones to be exerted when the extension unit 92 is attached to the output switching unit. The description of the operations will therefore be omitted.

The present embodiment provides the advantage described below.

According to the present embodiment, the number of ports which are disposed on the output switching unit and to which handpieces are plugged in can be set to any value. Consequently, the components of a system can be arranged neatly within a limited operating space.

According to the third and fourth embodiments, energy can be propagated to a selected intended handpiece without the necessity of removing a plurality of handpieces from a region to be operated on during an operation. This leads to highly improved operating efficiency.

(Fifth Embodiment)

A fifth embodiment of the present invention will be described with reference to FIG. 14 to FIG. 16. An object of the present embodiment is to provide an endoscopic surgical operation system making it possible to readily and reliably select any of a plurality of types of handpieces for use without being distracted from a lesion to be treated. The background of the present embodiment will be described below.

Japanese Unexamined Patent Publication No. 2000-271135 has disclosed a switching means for feeding ultrasonic energy, which is generated by one apparatus (ultrasonic operation apparatus), selectively to a plurality of handpieces. Herein, a connector expansion unit is connected between an ultrasonic treatment handpiece and the ultrasonic operation apparatus.

Assuming that the foregoing components are used in combination with a plurality of handpieces to perform an operation, it is unnecessary to replace a handpiece connected to the ultrasonic operation apparatus with another every time a handpiece to be used is changed to another. The connector expansion unit switches the handpieces to make one handpiece usable.

Moreover, the connections through the switching means can be switched using a selection switch disposed on the connector expansion unit or a hand-held switch.

However, according to the Japanese Unexamined Patent Publication No. 2000-271135, a selected handpiece cannot be identified until energy is actually output.

Moreover, a means for checking if a selected switch is associated with an intended handpiece must judge whether the handpiece and ultrasonic operation apparatus are actually connected to each other over a cable.

Therefore, every time an operator who uses handpieces changes the handpieces, the operator has to turn his/her eyes from a living tissue to be treated to the apparatus. The present embodiment attempts to resolve this drawback.

The present embodiment is analogous to the first embodiment. The same reference numerals will be assigned to components identical to those of the first embodiment, and the description of the components will be omitted.

A surgical operation system 1B in accordance with the present embodiment is different from the system 1 shown in FIG. 1 in a point that a main apparatus 2B having another ability added thereto is substituted for the main apparatus 2 and an endoscope system 129 is included.

The endoscope system 129 consists mainly of an optical endoscope (hereinafter endoscope) 130, a camera head 131, a light source unit 133, a camera control unit (hereinafter CCU) 135, and a monitor 136. The endoscope 130 enables endoscopic examination. The camera head 131 is mounted on the endoscope 130. An imaging device for producing an endoscopic image is incorporated in the camera head 131. The light source unit 133 supplies illumination light to the endoscope 130 over a light guide cable 132. The CCU 135 is connected to the camera head 131 over a signal cable 134, and processes a signal sent from the imaging device to produce a video signal. The monitor 136 is connected to the CCU 135 and displays an endoscopic image. Herein, the CCU 135 is connected to the main apparatus 2B over a communication cable 137.

Figure 15:
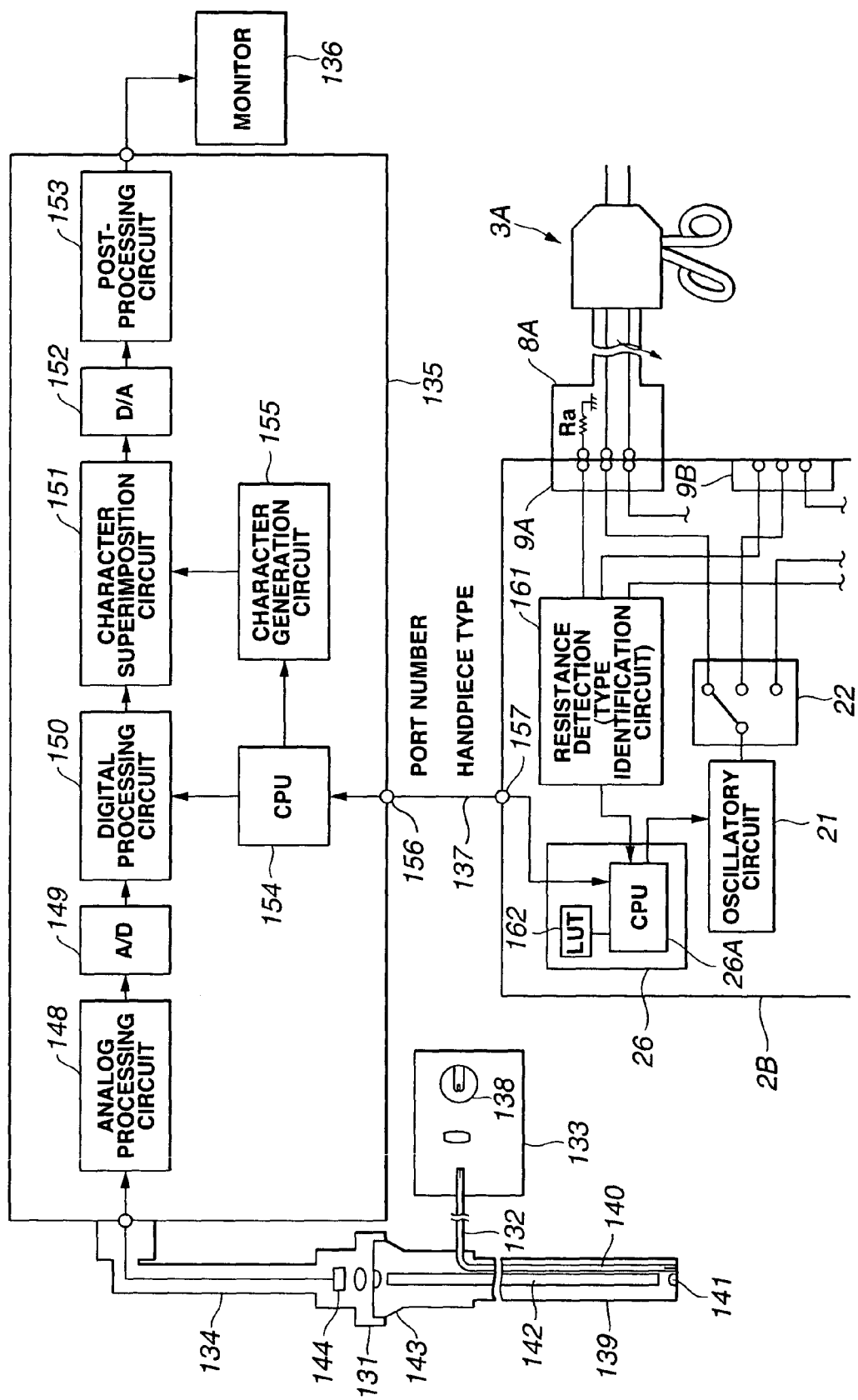

FIG. 15 shows the CCU 135 included in the endoscope system 129 and part of the main apparatus 2B.

The light source unit 133 has a built-in light source lamp 138. Illumination light emanating from the light source lamp 138 is converged and propagated over the light guide cable 132. The illumination light is further propagated over a light guide 140 that runs through an insertion unit 139 included in the endoscope 130, and emitted from the distal end of the endoscope 130.

An optical image of an illuminated object such as a lesion is initially passed through an objective 141, and then propagated through a relay lens system 142. The optical image is picked up by the imaging device 144 incorporated in the camera head 131 mounted on an eyepiece unit 143.

A signal resulting from photoelectric conversion performed by the imaging device 144 is transferred to an analog processing circuit 148 included in the CCU 135 over the signal cable 134. After subjected to analog processing such as amplification and color separation, the signal is converted into a digital form by an A/D conversion circuit 149.

The signal is subjected to white balance control or the like by a digital processing circuit 150, and then transferred to a character superimposition circuit 151. A digital video signal output from the character superimposition circuit 151 is converted into a standard video signal via a D/A conversion circuit 152 and a post-processing circuit 153, and transferred to the monitor 136.

Moreover, a CPU 154 is included in the CCU 135, and controls, for example, the digital processing circuit 150 included in the CCU 135.

Moreover, a character generation circuit 155 is included in the CCU 135, generates characters according to a control signal sent from the CPU 154, and communicates them to the character superimposition circuit 151.

The CPU 154 is connected to a CPU 26A included in the control circuit 26 through a connector 157 formed on the main apparatus 2B over the communication cable 137 that has one end thereof spliced to a connector 156. The CPU 154 transfers information to or from the CPU 26A.

The main apparatus 2B is different from the main apparatus 2 shown in FIG. 2 in a point that a resistance detection (type identification) circuit 161 is included for detecting the resistance of a type identification resistor Ri included in each handpiece 3I, and thus identifying the type of handpiece. In FIG. 15, the handpiece 3A is plugged in to the connector 9A, the resistance of the type identification resistor incorporated in the handpiece 3A shall be denoted as Ra.

The resistance detection circuit 161 has three input terminals thereof connected to the type identification resistors Ri through contacts in the connectors 9A to 9C. The resistors Ri are connected to contacts in the connectors 8I. The resistance detection circuit 161 senses a resistance associated with the type of handpiece 3I that is plugged in to the connector 9A, 9B, or 9C.

The resistance detected by the resistance detection circuit 161 is communicated to the CPU 26A. The CPU 26A references a lookup table (LUT) 162, in which identification information is written in advance, to judge with what handpiece type the detected resistance is associated. Instead of detecting the resistance, a reference voltage may be divided by a known resistance and the resistance of the type identification resistor Ri, and a handpiece type may be judged from the resultant fractions of the voltage.

In FIG. 15, the scissors-like handpiece 3A plugged in to the connector 9A (port A) is identified. The CPU 26A records in a register within the CPU 26A the identified handpiece type and the port number of the port to which the handpiece is plugged in.

Moreover, when the selection switch 10I on the main apparatus 2B or the remote switch 5 is pressed in order to select the handpiece 3I to be used, a port I to which the handpiece is plugged in is communicated to the CPU 26A in the control circuit 26.

When it is thus instructed to select the handpiece 3I, the CPU 26A transfers the handpiece type indicating the type of handpiece 3I and the port number, which are recorded in the register, to the CPU 154. The handpiece type and port number are then, as shown in FIG. 16, indicated on the display screen of the monitor 136.

When an operator holds the handpiece 3I the operator wants to use instead of pressing the selection switch 10I or the like to instruct selection of a handpiece, the port I to which the handpiece 3I is plugged in is detected by the sensor circuit 24I and communicated to the CPU 26A in the control circuit 26.

Even in this case, the CPU 26 A transfers the handpiece type and port number to the CPU 154. The handpiece type and port number are then indicated on the display screen of the monitor 136.

As described in relation to the first embodiment, when the handpiece 3I is held, the contacts i of the selector switch 22 are switched so that a driving signal can be applied to the port I selected by the selection circuit 25.

In the present embodiment, when the handpiece 3I is selected or held, the routes of the output line extending from the oscillatory circuit are switched so that a driving signal can be, as described in relation to the first embodiment, applied to the port I to which the handpiece 3I is plugged in. The type of handpiece 3I and the port number of the port I are indicated on the monitor 136.

An operator checks the type of handpiece 3I selected or held while viewing an endoscopic image displayed on the display screen of the monitor 136. The operator need not turn his/her eyes to the main apparatus 2B to check the selected handpiece. That is to say, even when a plurality of handpieces is used, a selected or held handpiece can be identified reliably without the necessity of turning eyes. This leads to improved maneuverability.

Major operations to be exerted by the present embodiment will be described briefly.

Figure 14:
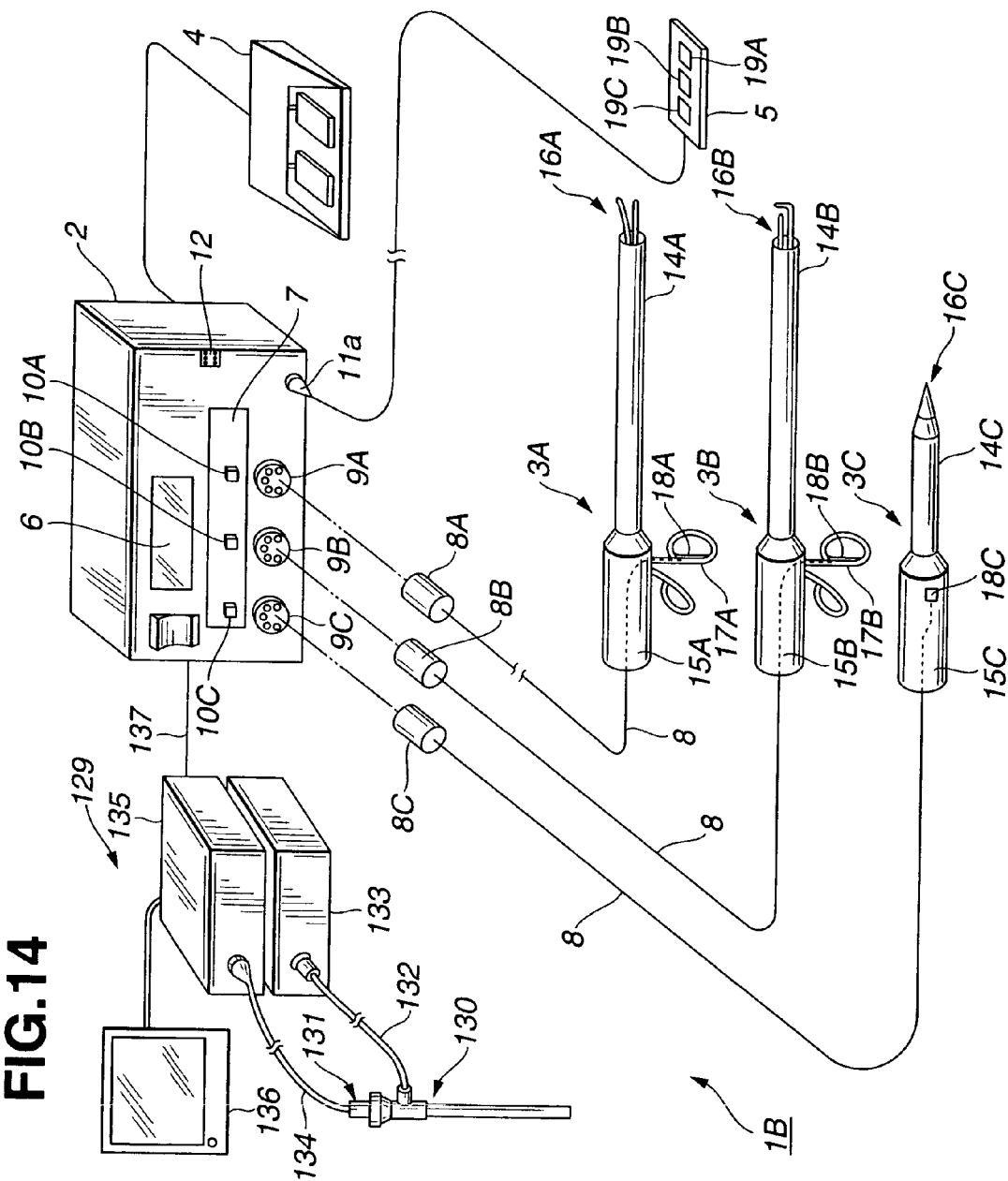
FIG. 14 to FIG. 16 are concerned with a fifth embodiment of the present invention.

When a surgical procedure is performed under endoscopic observation, the endoscope system 129 is prepared as shown in FIG. 14. Moreover, the communication cable 137 extending from the CCU 135 is coupled to the main apparatus 2B.

Moreover, a plurality of handpieces or a single handpiece that is intended to be used during the surgical procedure is connected to the main apparatus 2B.

For example, when the scissors-like handpiece 3A is, as shown in FIG. 15, plugged in to the port A (connector 9A) formed on the main apparatus 2B, the resistance detection circuit 161 senses the resistance of the type identification register Ra incorporated in the connector 8A. The resistance is communicated to the CPU 26A. The CPU 26A references the lookup table 162 to check the identification information written therein, and judges that the scissors-like handpiece 3A has been plugged in to the port A. The CPU 26A stores the information in the internal register or the like.

When the hook-like handpiece 3B is plugged in to the connector 9B, the CPU 26A judges that the hook-like handpiece 3B has been plugged in to the port B, and stores the information.

The endoscope 130 and handpiece 3A are inserted into the patient's abdomen using a trocar that is not shown, whereby a lesion is observed. An endoscopic image of the lesion is displayed on the display screen of the monitor 136. An operator views the endoscopic image. When the operator holds, for example, the scissors-like handpiece 3A for use during an operation, a detection signal associated with the held state is transferred to the sensor circuit 24A as described in relation to the first embodiment.

Based on the detection signal, the sensor circuit 24A transmits a selection signal, which indicates that the handpiece 3A is held, to the selection circuit 25. The selection circuit 25 recognizes that it has received the selection signal from the sensor circuit 24A out of the plurality of sensor circuits 24A, 24B, and 24C.

Consequently, the selection circuit 25 transmits a switching control signal to the selector switch 22 so that the output line extending from the oscillatory circuit 21 will be routed to the connector 9A to which the held handpiece 3A is plugged in. The result of selection performed by the selection circuit 25 is communicated to the CPU 26A in the control circuit 26, presented on the operator display panel 6, and notified using the loudspeaker 12.

Moreover, when the result of selection performed by the selection circuit 25 is communicated to the CPU 26A, the CPU 26A communicates the selected handpiece type and port number to the CPU 154 in the CCU 135 over the communication cable 137.

The CPU 154 causes the character generation circuit 155 to generate characters associated with the received information. The characters are communicated to the character superimposition circuit 151, and superimposed on the endoscopic image. A video signal representing the endoscopic image on which the characters are superimposed is transferred to the monitor 136. Consequently, the held handpiece type and port number are, as shown in FIG. 16, indicated with the endoscopic image displayed on the display screen of the monitor 136.

Figure 16:
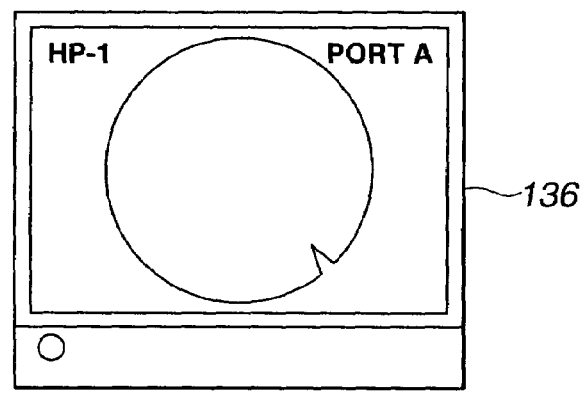

Referring to FIG. 16, HP-1 is displayed to indicate the handpiece type, and Port A is displayed to indicate the port number.

Therefore, an operator can check the type of held handpiece 3A and the output port to which the handpiece is plugged in while viewing the endoscopic image displayed on the monitor 136, but will not be distracted from the endoscopic image.

After checking the type of handpiece 3A and the output port, the operator may step on the footswitch 4 to turn on the footswitch 4. Consequently, ultrasonic energy is output from the distal end of the selected handpiece 3A, and incision or any other treatment can be carried out.

After the scissors-like handpiece 3A is used to perform treatment, the scissors-like handpiece 3A may be released and the hook-like handpiece 3B may be held instead. In this case, the routes of the output line extending from the oscillatory circuit are switched so that the output line will be routed to the handpiece 3B. Moreover, the handpiece type (for example, HP-2) and the port number (for example, Port B) are indicated on the monitor 136.

When the trocar-like handpiece 3C is held, the same indications are displayed.

The selection switch 10I located on the operator panel 7 or the selection switch 19I included in the remote switch 5 may be pressed instead of holding the handpiece 3A or pressing. In this case, the selection circuit 25 switches the contacts of the selector switch 22. Even in this case, the type of selected handpiece and a port number to which the handpiece is plugged in are indicated on the monitor 136.

According to the present embodiment, even when an operator wants to perform a surgical procedure using ultrasonic treatment appliances while viewing an endoscopic image, the type of ultrasonic treatment appliance plugged in to each port is identified and indicated on the screen of the monitor on which the endoscopic image is displayed. The operator can identify the type of ultrasonic treatment appliance actually plugged in to each port without turning his/her eyes from the viewed endoscope. The present embodiment provides an environment in which an operation can be performed smoothly.

In the present embodiment, when a handpiece to be used is held, the system is set to a mode in which the handpiece is used to perform treatment. An operator can therefore more easily continue a cure without looking away from a tissue being treated than when the operator designates a handpiece using the hand-held switch.

Moreover, an operator can select a handpiece by himself/herself in a clean zone.

According to the aforesaid constituent features, two sets of characters can be displayed. Alternatively, one set of characters alone may be displayed. However, at least one set of characters should be displayed.

When the two kinds of information are presented, if two handpieces of the same type are prepared for use, either of the handpieces now selected for use can be identified based on a port number indicated.

(Sixth Embodiment)

Figure 18:
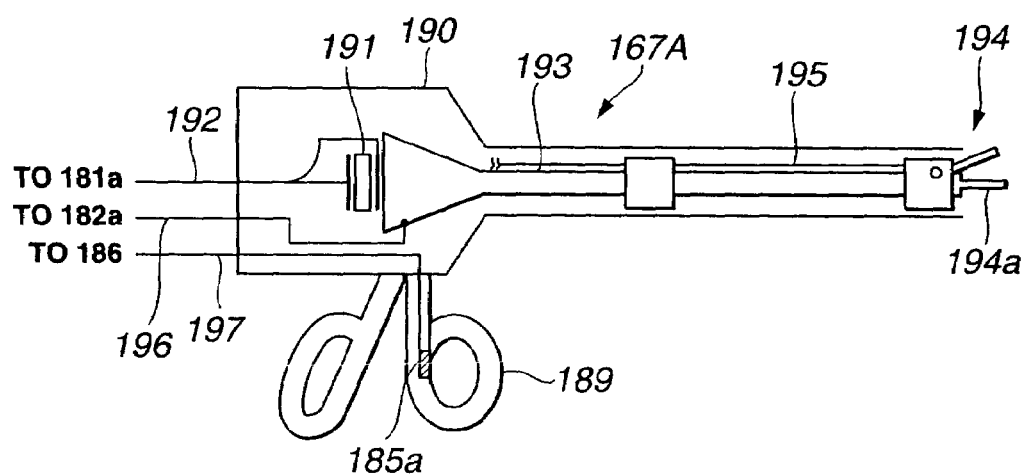

Next, a sixth embodiment of the present invention will be described with reference to FIG. 17 and FIG. 18. A high-frequency/ultrasonic surgical operation system 161 in accordance with the sixth embodiment shown in FIG. 17 is analogous to the high-frequency/ultrasonic surgical operation system 61 in accordance with the third embodiment shown in FIG. 10.

The high-frequency/ultrasonic surgical operation system 161 has a counter electrode plate 164 interposed between an operating table 162 and a patient 163 who lies down on the operating table 162.

The counter electrode plate 164 is connected to a high-frequency generator 165 over a cable. A rigid endoscope 166, a scissors-like handpiece 167A, a rod-like handpiece 167B, and a hook-like handpiece 167C are inserted in the abdomen of the patient 163 through a sheath that is not shown.

The scissors-like handpiece 167A, rod-like handpiece 167B, and hook-like handpiece 167C have nearly the same structures as those described in conjunction with FIG. 11A, FIG. 11B, and FIG. 11C. Treatment using ultrasonic waves and treatment using a high-frequency electric signal can be carried out. Moreover, the present embodiment includes hold detection sensors 185*a*, 185*b*, and 185*c* that will be described later.

A TV camera head 171 having a built-in imaging device is mounted on the back end of the rigid endoscope 166. The TV camera 171 is connected to a CCU 172 that processes a signal produced by the imaging device. A standard video signal produced by the CCU 172 is transferred to a TV monitor 173, whereby an endoscopic image picked up by the imaging device is displayed on the display screen of the TV monitor 173.

The scissors-like handpiece 167A, rod-like handpiece 167B, and hook-like handpiece 167C are connected to the high-frequency generator 165 and an ultrasonic generator 175 via an output switching unit 174 that switches the routes of an output line extending from each of the generators.

The high-frequency generator 165 and ultrasonic generator 175 are connected to footswitches 176 and 177 respectively. Output of high-frequency energy or ultrasonic energy can be started or stopped by turning on or off the footswitch 176 or 177.

Moreover, the output switching unit 174 has, for example, three ports a, b, and c formed thereon. A remote switch 179 including port selection switches 178*a*, 178*b*, and 178*c* used to select the ports a, b, and c respectively is connected to the output switching unit 174.

The three ports a, b, and c are composed of ultrasonic ports 181*a*, 181*b*, and 181*c* and high-frequency ports 182*a*, 182*b*, and 182*c*. The handpieces 167A, 167B, and 167C are plugged in to the ports.

To be more specific, an ultrasonic connector attached to a cable extending from the scissors-like handpiece 167A is joined with the ultrasonic port 181*a* on the output switching unit 174. An active-cord mechanism contained in the cable is spliced to the high-frequency port 182*a*.

An ultrasonic connector attached to a cable extending from the rod-like handpiece 167B is joined with the ultrasonic port 181*b* formed on the output switching unit 174. An active-cord mechanism contained in the cable is spliced to the high-frequency port 182*b*. An ultrasonic connector attached to a cable extending from the hook-like handpiece 167C is joined with the ultrasonic port 181*c* formed on the output switching unit 174. An active-cord mechanism contained in the cable is spliced to the high-frequency port 182*c*.

The output switching unit 174 switches the routes of a driving output line extending from the generator 165 or 175 so that the driving output line will be routed to the port i to which the handpiece 167I is plugged in.

Moreover, the output switching unit 174 has selection indicators 183*a*, 183*b*, and 183*c*, each of which indicates that the port a, b, or c has been selected, formed thereon.

In the present embodiment, the handpieces 167A, 167B, and 167C are provided with hold detection sensors 185*a*, 185*b*, and 185*c* each of which detects (or recognizes) that the handpiece 167A, 167B, or 167C is held.

To be more specific, the scissors-like handpiece 167A has the sensor 185*a* embedded in the operator handle thereof. The rod-like handpiece 167B and hook-like handpiece 167C have the sensors 185*b* and 185*c* respectively embedded on the peripheries of the hand-held members thereof with which an operator hold the handpieces.

Outputs of the sensors 185*a* to 185*c* are transferred to a hold detector 186. The hold detector 186 transmits a signal, with which a handpiece detected to be held is selected, to the output switching unit 174. The held handpiece is then made usable.

Moreover, the output switching unit 174 is connected to a CPU 187 included in the CCU 172 over a communication cable. The output switching unit 174 transmits information of the port i, to which the handpiece 167I detected to be held by the hold detector 186 is plugged in, to the CPU 187. The CPU 187 controls a character generating means included in the CCU 172, superimposes characters on an endoscopic image displayed on the monitor 173, and thus indicates the port i to which the selected handpiece is plugged in.

As mentioned above, the handpieces 167A to 167C have nearly the same structures as those described in conjunction with FIG. 11A to FIG. 11C. For example, the scissors-like handpiece 167A is structured as roughly shown in FIG. 18.

An ultrasonic transducer 191 to be ultrasonically oscillated is stowed in an operator unit 190 from which an operator handle 189 is projected. An ultrasonic driving signal is applied to the ultrasonic transducer 191 over an ultrasonic driving line 192. Ultrasonic oscillations produced by the ultrasonic transducer 191 are propagated to a stationary blade 194a included in a distal treatment member 194 over an ultrasound propagation rod 193, thus causing the stationary blade 194a to oscillate.

When the handpiece 167A is held with the operator handle 189 and the operator handle 189 is opened or closed, the movement of the operator handle is conveyed to the distal end of the ultrasound propagation rod 193 over an operation wire 195. This causes a movable blade included in the treatment member 194 to pivot. Ultrasonic waves are applied to a tissue clamped by the stationary blade 194a and movable blade, whereby the tissue is resected.

Moreover, the ultrasound propagation rod 193 is electrically coupled to a high-frequency output line 196. High-frequency current flows along the ultrasound propagation rod 193 after passing through the high-frequency output line 196. The high-frequency current then flows into a tissue via the stationary blade 194a, whereby the tissue is treated with high-frequency power.

Moreover, the operator handle 189 has the sensor 185a. The sensor 185a is connected to the hold detector 186 over a sensor line 197.

The other components are identical to those described in relation to the third embodiment and fifth embodiment.

The present embodiment provides the same advantages as the third embodiment does. In addition, the port i to which the held handpiece 167I is plugged in is indicated on the monitor 173.

Next, operations to be exerted by the present embodiment will be described briefly.

The components of the system are connected to one another as shown in FIG. 17. An operator inserts the rigid endoscope 166, scissors-like handpiece 167A, rod-like handpiece 167B, and hook-like handpiece 167C in the body of the patient 163, and observes the distal parts of the handpieces using the rigid endoscope 166. Namely, an image to be viewed owing to the rigid endoscope 166 is converted into an electrical signal by the TV camera head 171, and the electrical signal is converted into a standard video signal by the CCU 172. Eventually, the image is displayed on the display screen of the TV monitor 173.

While viewing the image on the TV monitor 173, the operator holds, for example, the scissors-like handpiece 167A out of the handpieces 167A to 167C so as to move the handpiece to a desired position in an region to be operated on.

The hold causes an output of the sensor 185 to change. The hold detector 186 detects that the sensor 185a embedded in the scissors-like handpiece 167A is blocked with the fingers of a hand holding the handpiece. The hold detector 186 then transmits an associated detection signal to the output switching unit 174.

The output switching unit 174 causes the driving output line extending from the generator 165 or 175 to conduct electricity to the port a to which the scissors-like handpiece 167A is plugged in. At this time, the selection indicator 183a is lit to indicate that the port a has been selected.

In this state, when the footswitch 176 or 177 is turned on, driving energy generated from the generator 165 or 175 is output to the handpiece 167A plugged in to the port a.

A signal sensed by the hold detector 186 is sent to the CPU 187 in the CCU 172 via the output switching unit 174. The CPU 187 instructs generation of characters indicating the sensed port a. Consequently, the indication of the port a is displayed on the monitor 173 as shown in FIG. 17.

While viewing an endoscopic image, an operator can discern that the port a to which the handpiece 167A is plugged in has been selected without the necessity of turning his/her eyes to the output switching unit 174 to check if the port a has been selected.

The same applies to a case where the other handpiece 167B or 167C is held.

The above description has been made on the assumption that the handpiece is held. Alternatively, the remote switch 179 may be manipulated. For example, when the port selection switch 178a is pressed, similarly to when the handpiece 167A is held, the routes of the output line extending from the generator are switched, and the indication of the port a is displayed.

The present embodiment provides the same advantages as the third embodiment does. In addition, one of the plurality of handpieces 167A to 167C held by an operator can be identified based on a press of the remote switch 179 or by the hold detector 186, and thus internally selected. The result of selection is communicated to the CCU 172. The information of a port to which the selected handpiece is plugged in is superimposed on an endoscopic image displayed on the display screen of the TV monitor 173. The operator can therefore identify the handpiece to be used without turning his/her eyes from the viewed endoscopic image.

(Seventh Embodiment)

Next, a seventh embodiment of the present invention will be described with reference to FIG. 19 to FIG. 23.

In the present embodiment, a plurality of handpieces (serving as surgical appliances) is simultaneously connected to a main apparatus. An external hand switch or a built-in hand switch is pressed to select a handpiece to be used. The selected handpiece and whether the handpiece is active are indicated on a monitor.

Figure 19:
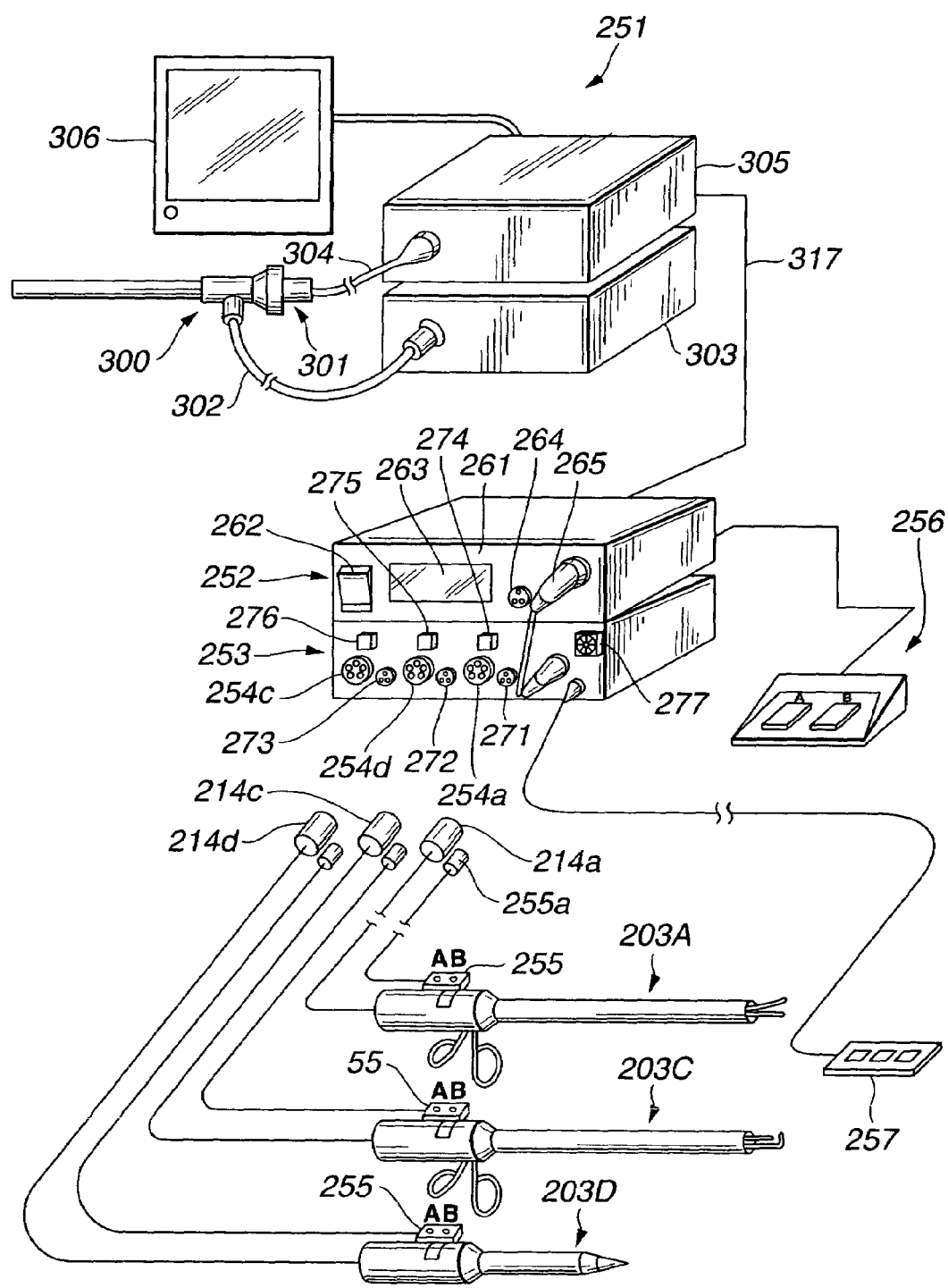
FIG. 19 to FIG. 23 are concerned with a seventh embodiment of the present invention.

As shown in FIG. 19, an ultrasonic operation system 251 in accordance with the seventh embodiment of the present invention consists mainly of a main apparatus 252, an expansion unit 253, a scissors-like handpiece 203A, a hook-like handpiece 203C, a trocar-like handpiece 203D, external hand switches 255, a footswitch 256, a remote switch 257, an optical endoscope (hereinafter endoscope) 300, a camera head 301, a light source unit 303, a camera control unit (hereinafter CCU) 305, and a monitor 306. The main apparatus 252 has a driving means, which generates a driving signal as described later, incorporated therein. The driving signal sent from the driving means incorporated in the main apparatus 252 is transferred to the expansion unit 253. The scissors-like handpiece 203A, hook-like handpiece 203C, and trocar-like handpiece 203D are plugged in to output ports (output terminals) formed on the expansion unit 253 so that they can be unplugged freely. The external hand switches 255 are freely detachably attached to the lateral parts of the operator units of the handpieces. The footswitch 256 and external hand switches 255 are selectively used. The remote switch 257 is connected to the expansion unit 253 so that it can be disconnected freely, and used to remotely select the output port 254a, 254b, or 254c. The endoscope 300 enables endoscopic examination. The camera head 301 is mounted on the endoscope 300 and has a built-in imaging device that picks up an endoscopic image. The light source unit 303 supplies illumination light to the endoscope 300 over a light guide 302. The CCU 305 is connected to the camera head 301 over a signal cable 304, and processes a signal produced by the imaging device to produce a video signal. The monitor 306 is connected to the CCU 305 and displays an endoscopic image.

Handpiece plugs 214a, 214c, and 214d attached to cables extending from the scissors-like handpiece 203A, hook-like handpiece 203C, and trocar-like handpiece 203D are joined with the output ports 254a, 254b, and 254c respectively. Any of the handpieces can be selected for use.

Figure 21:
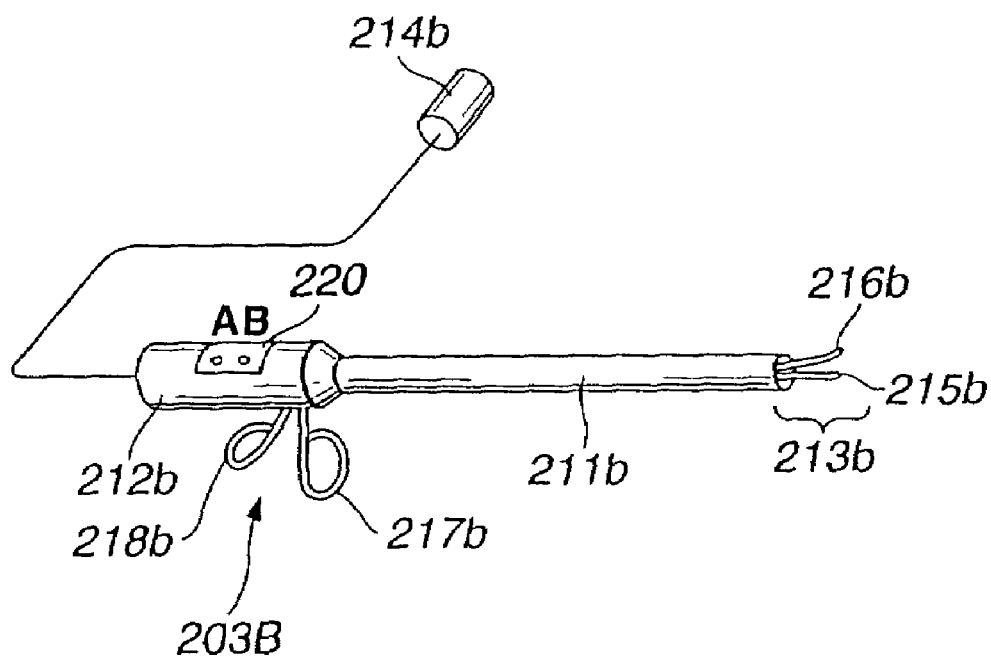

A handpiece plug 214b attached to a cable extending from the scissors-like handpiece 203B in which a built-in hand switch 220 is mounted as shown in FIG. 21 can be joined with an output port on the expansion unit 253 so that the handpiece plug can be disjoined freely. The scissors-like handpiece 203B consists mainly of an elongated sheath 211b, an operator unit 212b, and a treatment member 213b. The operator unit 212b communicates with the proximal end of the sheath 211b and is designed to lie near an operator's hand. The treatment member 213b is projected from the distal end of the sheath 211b.

The treatment member 213b has a clamping piece 216b that is supported at the distal end of the sheath 211b so that it can pivot freely. The clamping piece 216b approaches to or parts from the distal part of a probe 215b that runs through the sheath 211b. The operator unit 212b includes a stationary handle 217b and a movable handle 213b. When the movable handle 218b is opened or closed relative to the stationary handle 217b, the clamping piece 216b of the treatment member 213b can be approached to or parted from the distal part of the probe 215b. The scissors-like handpiece 203A shown in FIG. 19 has the same structure.

As shown in FIG. 19, a front panel 261 of the main apparatus 252 has a power switch 262, a display panel 263, and a hand switch connector 264 formed thereon. The display panel 263 is used to indicate whether a handpiece is active. Plugs attached to cables extending from the external hand switches 255 can be joined with the hand switch connector 264 so that they can be disjoined freely.

A rear panel of the main apparatus 252 (not shown in FIG. 19) has a footswitch connector 256b formed thereon. A footswitch plug 256a attached to a cable extending from the foot switch 256 is joined with the footswitch connector 256b so that it can be disjoined freely.

Moreover, an output port 252a formed on the main apparatus 252 is connected to an input port 253a formed on the expansion unit 253 over a joint cord 265. A driving signal sent from the driving means incorporated in the main apparatus 252 is transferred to the expansion unit 253 by way of the output port 252a, joint cord 265, and input port 253.

The expansion unit 253 has connectors 271, 272, and 273, selection switches 274, 275, and 276, and a remote switch connector 278. The connectors 271, 272, and 273 have the same ability as the hand switch connector 264 formed on the main apparatus 252. The connectors 255a attached to the cables extending from the external hand switches 255 are joined with the connectors 271, 272, and 273 so that they can be disjoined freely. The selection switches 274, 275, and 276 are used to manually select one of the output ports 254a, 254b, and 254c. The remote switch plug 257a attached to the cable extending from the remote switch 257 is joined with the remote switch connector 278 so that it can be disjoined freely.

Figure 20:
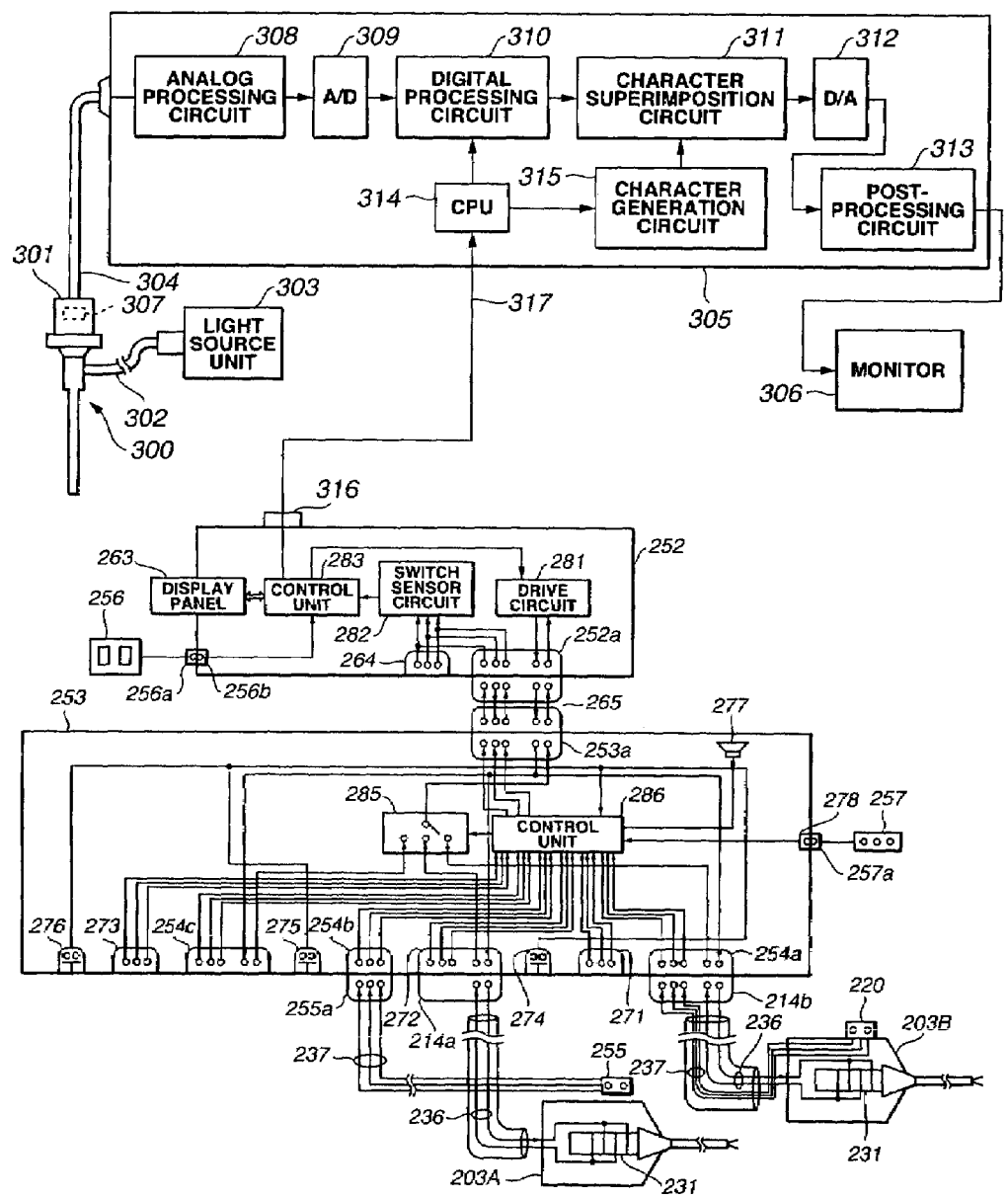

Moreover, the rear panel of the main apparatus 252 has, as shown in FIG. 20, a connector 316 through which an output terminal status signal is transmitted (via a control circuit 283 to be described later). The output terminal status signal is transmitted to the CCU 305 over a joint cord 317, whereby whether an actually selected output terminal is active is indicated on the monitor 306. This enables an operator to discern which of the handpieces has been selected and whether the selected handpiece is active.

The CCU 305 is designed to produce a video signal from a signal sent from a charge-coupled device (hereinafter CCD) incorporated in the camera head 301, and to display an endoscopic image on the monitor 306. On receipt of the output terminal status signal sent over the joint cord 317, whether a selected handpiece is active is indicated with the endoscopic image displayed on the monitor 306.

The present embodiment includes an output switching means for switching the output destinations of a driving signal, which is sent from the driving means incorporated in the main apparatus 252, according to a signal induced with a press of the external hand switch 255 or remote switch 257. Namely, the output switching means selects any of the output ports 254a, 254b, and 254c formed on the expansion unit 253.

Next, the circuitry of the ultrasonic operation system 251 in accordance with the present embodiment will be described in conjunction with FIG. 20.

The circuitry of the main apparatus 252 consists mainly of a drive circuit 281, a switch sense circuit 282, a display panel 263, and a control circuit 283.

The circuitry of the expansion unit 253 consists mainly of a relay 285 and a control circuit 286. The relay 285 switches the contacts thereof connected to the output ports 254a, 254b, and 254c formed on the expansion unit 253, and thus relays signal lines. The control circuit 286 controls switching of the contacts of the relay 285 according to a signal induced with a press of the built-in hand switch 220, external hand switch 255, or remote switch 257.

The control circuit 286 includes a latch or a memory that is not shown. When an output port is selected, the selected output port is recorded until another output port is selected. In the drawing, the scissors-like handpiece 203A, the scissors-like handpiece 203B having the built-in hand switch 220, the external hand switch 255, and the remote switch 257 are connected to the expansion unit 253.

When the built-in hand switch 220, external hand switch 255, or remote switch 257 is pressed, any of the output ports 254a, 254b, and 254c is selected. When a signal induced with the press is applied to the control circuit 286 included in the expansion unit 253, the control circuit 286 controls the relay 285 to close the contact of the relay 285 connected to the selected output port. Moreover, the selected output port is communicated to the switch sense circuit 282 in the main apparatus 252.

A selected handpiece alone out of the built-in hand switch 220 and external hand switches 255 is made usable. Each switch has two features of enabling start or stop of outputting energy and of enabling selection of a handpiece. This confuses an operator. For this reason, when both switches A and B included in each hand switch are pressed simultaneously, a signal for selecting an associated output port is induced. When the switches A and B are pressed separately, a signal for starting outputting a driving signal is induced.

To be more specific, when the switches A and B included in the built-in hand switch 220 or external hand switch 255 are pressed simultaneously, a signal induced is used to select any of the output ports 254a, 254b, and 254c. When the switches A and B are pressed separately, a signal induced is used to start or stop outputting a driving signal.

When any of the output ports 254a, 254b, and 254c is selected, which of the output ports has been selected is indicated on the display panel 263 under control of the control circuit 286 (via the switch sense circuit 282 and control circuit 283). At the same time, an output terminal status signal is transferred to the CCU 305 through the output connector 316.

The camera head 301 is connected to the CCU 305 over the signal cable 304. The CCD 301 is incorporated in the camera head 301, and photoelectrically converts an object image formed on the imaging surface of the CCD 307.

The endoscope 300 is a rigid endoscope such as a laparoscope employed in, for example, a surgical procedure. When the endoscope 300 is connected to the light source unit 303 over the light guide 302, illumination light emanating from the light source unit 303 is propagated over the light guide 302 and a light guide, which is not shown, running through the endoscope 300. The illumination light is then irradiated to an object through the distal end of the endoscope 300.

Light reflected from the illuminated object is converged and propagated by the endoscope 300. The CCD 307 incorporated in the camera head 301 picks up an optical image sent from the endoscope 300 and photoelectrically converts it.

An output signal of the CCD 307 in the camera head 301 is transferred to the CCU 305, and subjected to various kinds of signal processing by the CCU 305. In the CCU 305, the output signal of the CCD 307 is transferred to an analog processing circuit 308 and converted into a digital form by an A/D conversion circuit 309.

A digital processing circuit 310 performs white balance control or the like on a received signal, and transfers the signal to a character superimposition circuit 311. A digital video signal output from the character superimposition circuit 311 passes through a D/A conversion circuit 312 and a post-processing circuit 313. The digital video signal is thus converted into a standard video signal and transferred to the monitor 306.

The CPU 314 allows the CCU 305 to give various kinds of control. An output terminal status signal output through the output connector 316 formed on the main apparatus 252 is transmitted to the CCU 305 over the joint cord 317, and transferred to the CPU 314. In response to the output terminal status signal, the CPU 314 senses what output terminal is active, and gives an instruction to a character generation circuit 315. In response to a signal received from the CPU 314, the character generation circuit 315 communicates character information to the character superimposition circuit 311.

The character superimposition circuit 311 superimposes the character information on a digital video signal, and transfers the video signal to a signal processing stage that is a succeeding stage.

The thus configured ultrasonic operation system 251 is used to perform ultrasonic treatment. For example, the treatment member 213b of the scissors-like handpiece 203B having the built-in hand switch 220 mounted therein is brought into contact with a region to be treated within a living tissue. The built-in hand switch 220, external hand switch 255, or remote switch 257 is pressed in order to select an output port. Consequently, the selected output port and whether the port is active are, as shown in FIG. 22, indicated on the monitor 306.

Figure 22:
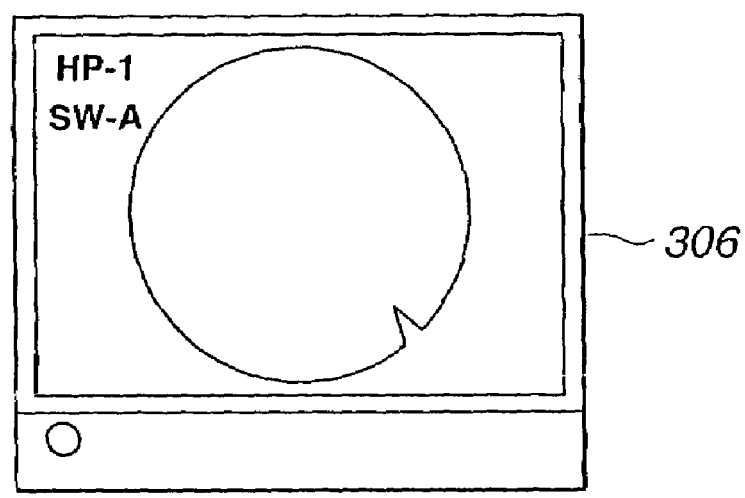

Referring Lo FIG. 22, HP-1 which indicates that the output port 1 through which energy is output to the first handpiece has been selected, and SW-A which indicates that the switch A has been selected are displayed adjacently to an endoscopic image on the monitor 106. Once an operator looks at the display screen of the monitor 306 in which the endoscopic image is displayed, the operator readily learns the selected handpiece and whether the handpiece is active while viewing the endoscopic image. The operator would find the ultrasonic operation system user-friendly.

Figure 23:
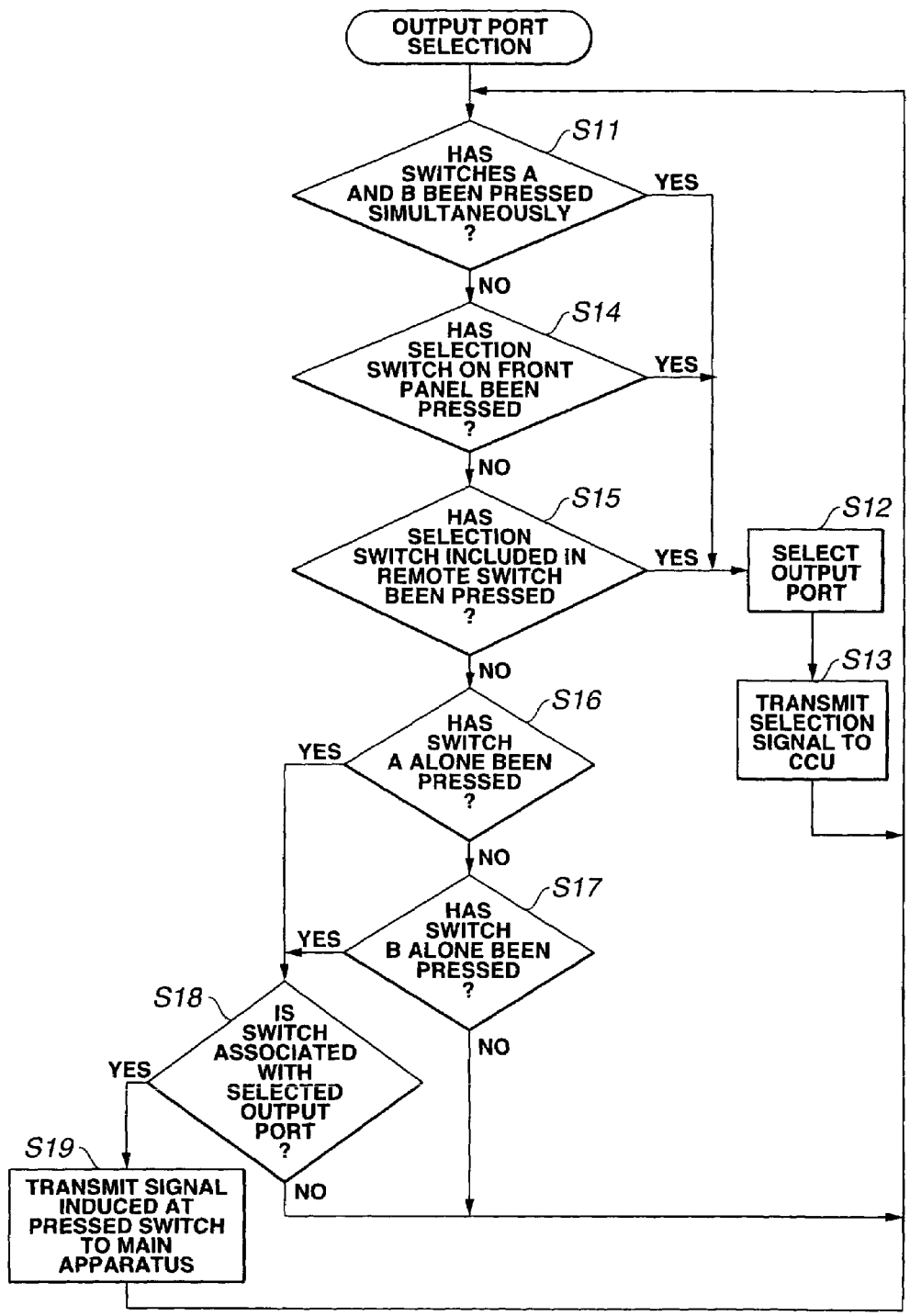

Selecting an output port using the built-in hand switch 220 or external hand switch 55 will be described in conjunction with FIG. 23.

For example, when the switch A (SW-A) and switch B (SW-B) included in the built-in hand switch 220 are pressed simultaneously, a signal induced is transferred to the control circuit 286 in the expansion unit 253. The fact that the switches A and B are pressed simultaneously is sensed (step S11). Control is then given to select the output port 254a (step S12).

For giving control to select the output port 254a, a signal for selecting the output port 254a is transferred to the switch sense circuit 282 in the main apparatus 252. Moreover, the relay 285 is controlled in order to close the contact of the relay 285 connected to the output port 254a.

The scissors-like handpiece 203B and the built-in hand switch 220 which are currently in use are indicated on the monitor 306 and the display panel 263 under control of the control circuit 283 in the main apparatus 252 (step S13).

When the selection switch 274 on the front panel 271 formed on the expansion unit 253 is pressed instead of simultaneously pressing the switches A and B included in the hand switch, a signal induced with the press is transferred to the control circuit 286 in the expansion unit 253. The press of the selection switch 274 is thus sensed (step S14), and control is given in order to select the output port 254a (step S12). The selected output port is indicated on the monitor 306.

Furthermore, when the selection switch associated with the output port 254a and included in the remote switch 257 is pressed, similarly to when the selection switch 274 on the expansion unit 253 is pressed, the press of the selection switch is sensed (step S15). Thereafter, as mentioned above, control is given in order to select an associated output port, and the selected output port is indicated.

On the other hand, when the switch A or switch B included in the built-in hand switch 220 is pressed independently, a signal induced with the press is transferred to the control circuit 286 in the expansion unit 253. The press of the switch A or switch B is sensed (step S16 or S17). It is judged whether the pressed switch A or B is associated with the already selected output port 254a (step S18). If so, a signal induced at the pressed switch A or B is transmitted to the main apparatus 252 (step S19).

For example, when the output port 254a is selected, a driving control signal is sent from the control circuit 283 in the main apparatus 252 to the drive circuit 281. The driving signal sent from the drive circuit 281 is applied to the handpiece 203B via the relay 285 through the selected output port 254a. Eventually, ultrasonic treatment is carried out.

Moreover, the fact that the driving signal has been applied to the handpiece 203B through the output port 254a is indicated on the display panel 263 under control of the control circuit 283, communicated to the CCU 305, and indicated on the monitor 306. For example, an indication is displayed in order to indicate that the switch A has been turned on. Moreover, when the switch B is turned off, an indication signifying that the switch B has been turned off is displayed (or nothing may be displayed).

Consequently, an operator in charge of an operation selects a handpiece the operator wants to use. This leads to improved maneuverability and enables the operator to concentrate on the operation. The operator can readily discern the selected handpiece and whether the handpiece is active. Moreover, when a handpiece is selected using the built-in hand switch 220, the two features of the switch of enabling start or stop of outputting energy and enabling selection of an output port can be utilized for different purposes without the necessity of including an additional hand switch line.

Furthermore, an operator can perform a surgical procedure while looking at the monitor 306 all the time. Even if the operator lies at a position at which the operator cannot look at the display panel 263 formed on the main apparatus 52 to check a result of switching the output ports, the operator can reliably discern whether a handpiece is active merely by looking at the monitor 306. The operator can proceed with the surgical procedure while enjoying user-friendliness.

(Eighth Embodiment)

Figure 24:
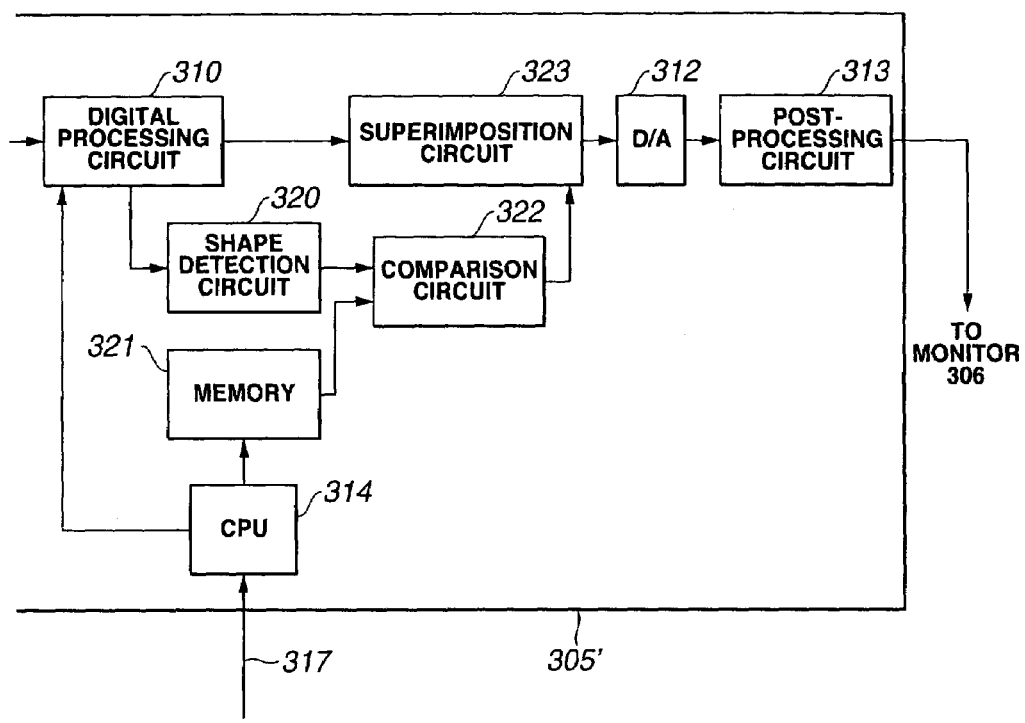
FIG. 24 and FIG. 25 are concerned with an eighth embodiment of the present invention.

Next, an eighth embodiment of the present invention will be described with reference to FIG. 24 and FIG. 25. The configuration of a system in accordance with the present embodiment is roughly the same as that of the system in accordance with the seventh embodiment. FIG. 24 shows part of a CCU.

In the present embodiment, the shapes of handpieces to be graphically indicated on the monitor 306 are recorded in advance in a memory. A pointing mark is displayed on the monitor 306. The pointing mark moves along with the movement of a handpiece.

The ultrasonic operation system in accordance with the present embodiment adopts a CCU 305' that is partly different from the CCU 305 shown in FIG. 20 and has the circuitry shown in FIG. 24.

To be more specific, the CCU 305' consists mainly of the digital processing circuit 310, the CPU 314, a shape detection circuit 320, a memory 321, a comparison circuit 322, and a superimposition circuit 323. The shape detection circuit 320 produces shape data from a digital video signal. The shapes of handpieces are recorded in advance in the memory 321. The comparison circuit 322 compares produced shape data with the shapes recorded in the memory 321, and determines the shape of a handpiece. Moreover, the comparison circuit 322 outputs position information. The superimposition circuit 323 displays a pointing mark on the monitor 306.

The circuits preceding the digital processing circuit 310 are identical to those employed in the seventh embodiment. Moreover, the circuits succeeding the D/A conversion circuit 312 to which an output signal of the superimposition circuit 323 is transferred are identical to those employed in the seventh embodiment. The description of the identical circuits will be omitted.

Similarly to the seventh embodiment, a signal produced by the CCD 307 is subjected to predetermined processing in the CCU 305', and transferred to the digital processing circuit 310.

A digital video signal is divided into two signal components.

A method of detecting a shape of a handpiece or a position thereof is described in, for example, Japanese Unexamined Patent Publication No. 8-164148. One of the two digital video signal components is transferred to the shape detection circuit 320.

The shape detection circuit 320 produces shape data including information of edges of an entity from the digital video signal, and transfers the data to the comparison circuit 322. The shapes of a plurality of handpieces are recorded in advance in the memory 321. In response to an instruction issued from the CPU 314, the shape detection circuit 320 produces shape data of a selected handpiece and sends it to the comparison circuit 322.

The comparison circuit 322 determines the shape of the selected handpiece according to the shape data sent from the shape detection circuit 320 by referencing the memory 321 in which the handpiece shapes are recorded. Furthermore, the comparison circuit 322 detects the position of the handpiece and transfers the position information to the superimposition circuit 323.

The superimposition circuit 323 superimposes a pointing mark (an encircled letter A in FIG. 25) on the distal part of a handpiece image according to the position information output from the comparison circuit 322. The handpiece image is contained in an endoscopic image represented by the digital video signal output from the digital processing circuit 310.

Figure 25:
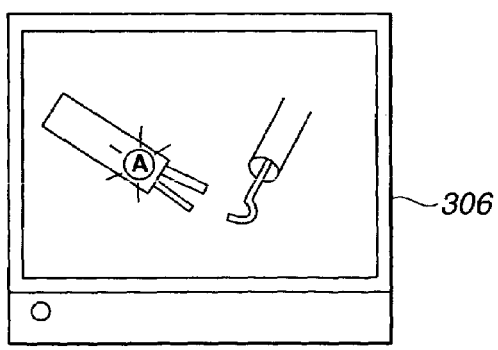

The pointing mark may be, as shown in FIG. 25, a symbol of A or B discriminating an output terminal. Alternatively, the pointing mark may be a color of blue or green associated with each output terminal.

Moreover, the CPU 314 receives an output terminal status signal, and records a selected output terminal in the memory 121.

As mentioned above, the pointing mark is superimposed on an image of a selected handpiece displayed on the monitor 306. The pointing mark follows the movement of the handpiece. When the selected output terminal is changed to another, the pointing mark is superimposed on an image of another handpiece selected.

Consequently, an operator intuitively discriminates a currently selected handpiece from among a plurality of handpieces. The other operations and advantages are identical to those of the seventh embodiment.

(Ninth Embodiment)

Next, a ninth embodiment of the present invention will be described with reference to FIG. 26 and FIG. 27.

According to the present embodiment, a keyboard of a personal computer is sealed with a sterilization cover so that it can be used in a clean zone to select a handpiece to be used.

Figure 26:
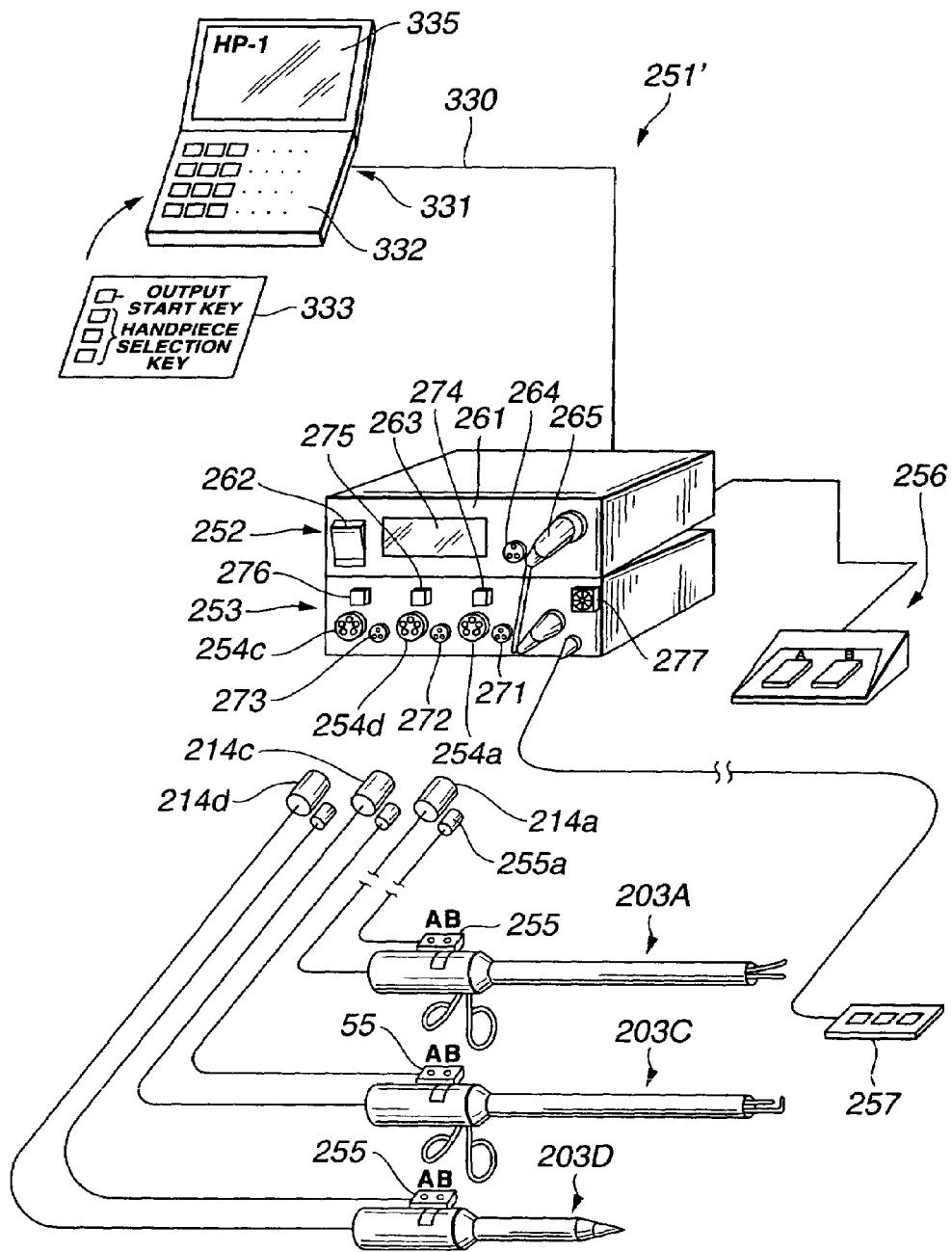

An ultrasonic operation system 251' shown in FIG. 26 is different from the ultrasonic operation system 251 shown in FIG. 19 in a point that a personal computer 331 is connected to the main apparatus 252 over a communication cable 330. Moreover, a keyboard 332 of the personal computer 331 is sealed with a sterilization cover 333 for use.

Symbols indicating a handpiece selection key, an output start key, and other keys are inscribed on the sterilization cover 333. An operator places the sterilization cover 33 on the keyboard 332 of the personal computer 331. The operator presses a predetermined key, whereby a control signal is transferred to the main apparatus 252 over the communication cable 330.

As shown in FIG. 27, one end of the communication cable 330 is spliced to a joint connector 334 formed on the main apparatus 252. The control signal is transferred to each of the control circuit 283 and switch sense circuit 282.

Consequently, the keyboard 332 is used in the same manner as the external hand switch 255 or the built-in switch of a handpiece which are employed in the seventh embodiment.

Moreover, a handpiece selected using the keyboard 332 and energy to be output are indicated on a display 335 of the personal computer 331.

According to the present invention, the keyboard 332 is used. The display 335 of the personal computer 331 may be sealed with a sterilization sheet so that the display 335 can be touched to enter a command.

Embodiments that can be constructed by partly combining the aforesaid embodiments shall belong to the present invention.

What is claimed is:

1. An endoscopic operation system comprising:
   an endoscope used to observe an intracorporeal region;
   a signal processor for processing an image signal, which is produced by an imaging device incorporated in the endoscope, to produce a video signal;
   an endoscopic image display device for displaying an endoscopic image, which is picked up by the imaging device, according to the video signal;
   a plurality of operating handpeices for generating treatment energies;
   a driving signal generator for generating a driving signal which causes any operating handpiece out of the plurality of operating handpieces to generate treatment energy;
   an output switching unit, connected between the driving signal generator and the plurality of operating handpieces, for switching the routes of an output line over which the driving signal is transmitted;
   hand-held members included in the plurality of operating handpieces and held for treatment;
   hold detecting devices, included in the hand-held members, the hold detecting devices each producing a predetermined hold detection signal when detecting that the hand-held member is held;
   an output switching control unit for receiving the hold detection signal, and controlling the output switching unit so that the output destinations of the driving signal will be switched to select an operating handpiece from which the hold detection signal is transmitted; and
   a superimposition unit for superimposing information of a handpiece, from which the hold detection signal is transmitted, on an image displayed on the endoscopic image display device.

2. An endoscopic operation system according to claim 1, wherein the operating handpieces are ultrasonic operation handpieces for generating ultrasonic energy as the treatment energy.

3. An endoscopic operation system according to claim 1, wherein the operating handpieces are high-frequency electric operation handpieces for generating high-frequency energy as the treatment energy.

4. An operation system comprising:
   a plurality of handpieces for generating predetermined energies, each of said handpieces including a hand-held member to be held for treatment and a hold detecting device which detects that the hand-held member is held, and a selection signal generator for generating a first selection signal which indicates that any of the handpieces has been selected,
   a driving signal generator generating a driving signal for driving any of said handpieces;
   an output switching unit for switching the output destination of the driving signal to the handpiece selected from the plurality of handpieces;
   a remote controller for generating a second selection signal, which indicates that any of the handpieces has been selected, to remotely control the output switching unit; and
   a switching control unit for controlling the output switching unit in response to one of the first and second selection signal so that the output destination of the driving signal will be switched to the selected handpiece, the selection signal generator further transmitting the selection signal to the switching control unit in response to a detection signal received from the hold detecting device which has detected that the hand-held member is held.

5. An operation system according to claim 4, further comprising:
   an imaging device for imaging a predetermined region to be observed;
   a signal processor for producing a predetermined video signal from an image signal produced by the imaging device;
   a display device for displaying a predetermined view image according to the video signal sent from the signal processor; and
   a superimposition unit for superimposing information of a handpiece, from which the selection signal is transmitted, on the view image displayed on the display device.

6. An operation system according to claim 5, wherein the superimposition unit superimposes on a video image displayed on the display device information of at least one of a type of handpiece from which the selection signal is transmitted.

7. An operation system according to claim 4, further comprising:
   a notifier for notifying information of the selected handpiece.

8. An energy-selective operation system according to claim 7, wherein the notifier notifies whether a selected handpiece is active.

* * * * *